United States Patent
Banno et al.

(10) Patent No.: US 10,975,043 B2
(45) Date of Patent: Apr. 13, 2021

(54) HETEROCYCLIC COMPOUND

(71) Applicant: TAKEDA PHARMACEUTICAL COMPANY LIMITED, Osaka (JP)

(72) Inventors: Yoshihiro Banno, Kanagawa (JP); Masahiro Kamaura, Kanagawa (JP); Kazuaki Takami, Kanagawa (JP); Koichiro Fukuda, Kanagawa (JP); Shigekazu Sasaki, Kanagawa (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 16/773,720

(22) Filed: Jan. 27, 2020

(65) Prior Publication Data
US 2020/0157062 A1    May 21, 2020

Related U.S. Application Data

(63) Continuation of application No. 16/230,634, filed on Dec. 21, 2018, now Pat. No. 10,544,111, which is a continuation of application No. 15/517,227, filed as application No. PCT/JP2015/079782 on Oct. 22, 2015, now Pat. No. 10,214,498.

(30) Foreign Application Priority Data

Oct. 24, 2014 (JP) ................. 2014-217770

(51) Int. Cl.
| | |
|---|---|
| A61K 31/4418 | (2006.01) |
| A61K 31/505 | (2006.01) |
| C07D 239/34 | (2006.01) |
| C07D 213/65 | (2006.01) |
| C07D 213/70 | (2006.01) |
| C07D 263/46 | (2006.01) |
| A61K 31/415 | (2006.01) |
| A61K 31/421 | (2006.01) |
| C07D 231/12 | (2006.01) |
| C07D 231/22 | (2006.01) |
| C07D 263/38 | (2006.01) |
| A61P 27/02 | (2006.01) |
| C07K 14/47 | (2006.01) |
| C12N 15/09 | (2006.01) |

(52) U.S. Cl.
CPC .......... *C07D 263/46* (2013.01); *A61K 31/415* (2013.01); *A61K 31/421* (2013.01); *A61K 31/4418* (2013.01); *A61K 31/505* (2013.01); *A61P 27/02* (2018.01); *C07D 213/65* (2013.01); *C07D 213/70* (2013.01); *C07D 231/12* (2013.01); *C07D 231/22* (2013.01); *C07D 239/34* (2013.01); *C07D 263/38* (2013.01); *C07K 14/47* (2013.01); *C12N 15/09* (2013.01)

(58) Field of Classification Search
None
See application file for complete search history.

(56) References Cited

U.S. PATENT DOCUMENTS

| | | | |
|---|---|---|---|
| 3,625,970 A | 12/1971 | Ambrus | |
| 5,239,080 A | 8/1993 | Sohda et al. | |
| 5,371,098 A | 12/1994 | Sohda et al. | |
| 8,338,622 B2 | 12/2012 | Kasai et al. | |
| 8,586,571 B2 | 11/2013 | Kasai et al. | |
| 8,853,215 B2 | 10/2014 | Kasai et al. | |
| 10,214,498 B2 | 2/2019 | Banno | |
| 10,544,111 B2* | 1/2020 | Banno | C07D 239/34 |
| 2004/0214788 A1 | 10/2004 | Raj et al. | |
| 2009/0088435 A1 | 4/2009 | Mata et al. | |
| 2010/0292206 A1 | 11/2010 | Kasai et al. | |
| 2011/0251187 A1 | 10/2011 | Kasai et al. | |
| 2012/0071489 A1 | 3/2012 | Kasai et al. | |

(Continued)

FOREIGN PATENT DOCUMENTS

| | | |
|---|---|---|
| CL | 201700992 | 11/2017 |
| CL | 201701001 | 11/2017 |

(Continued)

OTHER PUBLICATIONS

Search Report dated Feb. 11, 2019 in corresponding Chinese Application No. 201580057721.9 and its English Translation.

(Continued)

*Primary Examiner* — Zinna Northington Davis
(74) *Attorney, Agent, or Firm* — Jon E. Gordon; Haug Partners LLP

(57) ABSTRACT

Provided is a heterocyclic compound having a superior RBP4-lowering action and useful as a medicament for the prophylaxis or treatment of a disease or symptom mediated by an increase in RBP4 or retinol supplied by RBP4.
A compound represented by the formula (I):

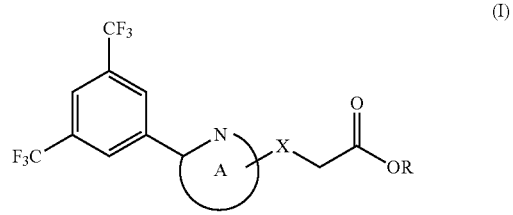

(I)

wherein each symbol is as defined in the Description, or a salt thereof has a superior RBP4-lowering action, and is useful as a medicament for the prophylaxis or treatment of a disease or symptom mediated by an increase in RBP4 or retinol supplied by RBP4.

2 Claims, No Drawings
Specification includes a Sequence Listing.

(56) References Cited

U.S. PATENT DOCUMENTS

| | | |
|---|---|---|
| 2012/0077854 A1 | 3/2012 | Petrassi et al. |
| 2014/0066420 A1 | 3/2014 | Kasai et al. |
| 2017/0190675 A1 | 7/2017 | Chen et al. |

FOREIGN PATENT DOCUMENTS

| | | |
|---|---|---|
| CN | 102112440 A | 6/2011 |
| CN | 102459203 A | 5/2012 |
| CN | 102459209 A | 5/2012 |
| EP | 2 295 406 A1 | 3/2011 |
| JP | 2010-540541 A | 12/2010 |
| JP | 2012-523461 A | 10/2012 |
| JP | 2012-524024 A | 10/2012 |
| WO | WO 2002/15920 A2 | 2/2002 |
| WO | WO 03/031984 | 4/2003 |
| WO | WO 2003/031984 A2 | 4/2003 |
| WO | WO 2004/085385 A2 | 10/2004 |
| WO | WO 2005/019184 A1 | 3/2005 |
| WO | WO 2005/059564 A1 | 6/2005 |
| WO | WO 2005/120583 A2 | 12/2005 |
| WO | WO 2006/007314 A1 | 1/2006 |
| WO | WO 2006/012521 A2 | 2/2006 |
| WO | WO 2006/042252 A2 | 4/2006 |
| WO | WO 2007/150046 A2 | 12/2007 |
| WO | WO 2009/002964 A1 | 12/2008 |
| WO | WO 2009/002970 A1 | 12/2008 |
| WO | WO 2009/051244 A1 | 4/2009 |
| WO | WO 2009/143390 A2 | 11/2009 |
| WO | WO 2009/145286 A1 | 12/2009 |
| WO | WO 2010/120741 A1 | 10/2010 |
| WO | WO 2011/059776 A2 | 5/2011 |
| WO | WO 2011/072275 A2 | 6/2011 |
| WO | WO 2011/126903 A2 | 10/2011 |
| WO | WO 2012/071369 A2 | 5/2012 |
| WO | WO 2012/154967 A1 | 11/2012 |
| WO | WO 2013/166041 A1 | 11/2013 |
| WO | WO 2014/134127 A1 | 9/2014 |
| WO | WO 2014/153643 A1 | 10/2014 |
| WO | WO 2014/160409 A1 | 10/2014 |
| WO | WO 2015/134973 A1 | 9/2015 |
| WO | WO 2016/063933 | 4/2016 |
| WO | WO 2016/172631 A2 | 10/2016 |

OTHER PUBLICATIONS

First Office Action dated Feb. 19, 2019 in corresponding Chinese Application No. 201580057721.9 and its English Translation.
Second Office Action dated Sep. 25, 2019 in corresponding Chinese Application No. 201580057721.9 and its English Translation.
Office Action dated Feb. 28, 2018 in corresponding Eurasian Application No. 201790912 and its English Translation.
Office Action dated Sep. 18, 2018 in corresponding Eurasian Application No. 201790912 and its English Translation.
Search Report dated Mar. 23, 2018 in corresponding European Application No. 15853151.7.
Office Action dated Jan. 29, 2019 in corresponding European Application No. 15853151.7.
Office Action dated Oct. 24, 2019 in corresponding European Application No. 15853151.7.
Substantive Examination Report mailed in corresponding Philippines Application No. 1-2017-500747, (2017).
Bioisosterism and Applications Thereof in the Design of Novel Drugs, OU Chunyan, Journal of Zhanjiang Ocean University, vol. 24, No. 4, Aug. 2004.
International Search Report and Written Opinion dated Jan. 19, 2016 in corresponding International Application No. PCT/JP2015/079782.
Examination Report No. 1 dated May 2, 2019 in corresponding Australian Application No. 2015336480.
Report No. 2 mailed in corresponding Chilean Application No. 0944-2017(dated Apr. 17, 2017).

* cited by examiner

```
                            SEQUENCE LISTING

<160> NUMBER OF SEQ ID NOS: 9

<210> SEQ ID NO 1
<211> LENGTH: 34
<212> TYPE: DNA
<213> ORGANISM: Artificial
<220> FEATURE:
<223> OTHER INFORMATION: PCR primer (RBPU)

<400> SEQUENCE: 1
atatggatcc accatgaagt gggtgtgggc gctc                              34

<210> SEQ ID NO 2
<211> LENGTH: 38
<212> TYPE: DNA
<213> ORGANISM: Artificial
<220> FEATURE:
<223> OTHER INFORMATION: PCR primer (RBPL)

<400> SEQUENCE: 2
atatgcggcc gcctacaaaa ggtttctttc tgatctgc                          38

<210> SEQ ID NO 3
<211> LENGTH: 35
<212> TYPE: DNA
<213> ORGANISM: Artificial
<220> FEATURE:
<223> OTHER INFORMATION: PCR primer (TTRU)

<400> SEQUENCE: 3
atatggatcc accatggctt ctcatcgtct gctcc                             35

<210> SEQ ID NO 4
<211> LENGTH: 35
<212> TYPE: DNA
<213> ORGANISM: Artificial
<220> FEATURE:
<223> OTHER INFORMATION: PCR primer (TTRL)

<400> SEQUENCE: 4
atatgcggcc gctcattcct tgggattggt gacga                             35

<210> SEQ ID NO 5
<211> LENGTH: 26
<212> TYPE: DNA
<213> ORGANISM: Artificial
<220> FEATURE:
<223> OTHER INFORMATION: PCR primer (CMVP)

<400> SEQUENCE: 5
tgggaggtct atataagcag agctcg                                       26

<210> SEQ ID NO 6
<211> LENGTH: 28
<212> TYPE: DNA
<213> ORGANISM: Artificial
<220> FEATURE:
<223> OTHER INFORMATION: PCR primer (RBPECO)

<400> SEQUENCE: 6
```

```
atatgaattc ttccttggga ttggtgac                                    28

<210> SEQ ID NO 7
<211> LENGTH: 30
<212> TYPE: DNA
<213> ORGANISM: Artificial
<220> FEATURE:
<223> OTHER INFORMATION: PCR primer (TTRECO)

<400> SEQUENCE: 7
atatgaattc caaaaggttt ctttctgatc                                  30

<210> SEQ ID NO 8
<211> LENGTH: 28
<212> TYPE: DNA
<213> ORGANISM: Artificial
<220> FEATURE:
<223> OTHER INFORMATION: oligonucleotide for preparation of synthetic
      gene fragment containing His tag sequence (HISENU)

<400> SEQUENCE: 8
aattccatca tcatcatcat cactaggc                                    28

<210> SEQ ID NO 9
<211> LENGTH: 28
<212> TYPE: DNA
<213> ORGANISM: Artificial
<220> FEATURE:
<223> OTHER INFORMATION: oligonucleotide for preparation of synthetic
      gene fragment containing His tag sequence (HISENL)

<400> SEQUENCE: 9
ggccgcctag tgatgatgat gatgatgg                                    28
```

HETEROCYCLIC COMPOUND

CROSS-REFERENCE TO RELATED APPLICATIONS

This application is a continuation of U.S. application Ser. No. 16/230,634 filed Dec. 21, 2018, which is a continuation of U.S. application Ser. No. 15/517,227 filed Apr. 6, 2017, now U.S. Pat. No. 10,214,498 issued Feb. 26, 2019, which is the National Stage entry under 35 U.S.C. § 371 of International Application No. PCT/JP2015/079782 filed Oct. 22, 2015, published as Publication No. WO/2016/063933 on Apr. 28, 2016, which claims priority on the basis of Japanese Patent Application No. 2014-217770 filed in Japan on Oct. 24, 2014, the entireties of which are all herein incorporated by reference.

TECHNICAL FIELD

The present invention relates to a heterocyclic compound useful as a medicament for the prophylaxis or treatment of a disease or condition mediated by an increase in RBP4 or retinol supplied by RBP4 such as age-related macular degeneration, Stargardt's disease and the like.

BACKGROUND OF THE INVENTION

It is known that retinol binding protein 4 (hereinafter sometimes to be abbreviated as "RBP4") is a sole blood retinol transfer protein mainly produced in the liver.

RBP4 forms a complex by binding to retinol and TTR (transthyretin) and is stably present in blood. When RBP4 is dissociated from TTR and becomes free, it is decomposed in and excreted from the kidney comparatively rapidly. It is unknown whether the binding of RBP4 and retinol is indeed essential for the formation of a complex with TTR. However, fenretinide, a retinol derivative, inhibits binding of RBP4 and retinol, and consequently inhibits formation of a complex with TTR. It is known that administration of fenretinide to an animal induces lowering of blood RBP4 (non-patent document 1).

The relationship between retinol supplied by RBP4 and ophthalmic diseases has been reported. For example, an excessive vitamin A level in the eye can induce various retina diseases including macular degeneration, and a decrease in RBP4 is effective for the prophylaxis or treatment of these ophthalmic diseases (patent document 1).

Fenretinide has been investigated in patients affected with geographic atrophy (GA), which is the most progressed form of atrophic age-related macular degeneration (AMD). Fenretinide has been suggested to discontinue accumulation of retinol (vitamin A) toxin via affinity to RBP4. It is assumed to delay formation and accumulation of toxicity by-products, for example, A2E (bis-retinoid pyridinium) considered to be involved in the loss of eyesight in diseases such as GA and the like. Sirion Therapeutics, Inc. publicly reported affirmative results of the analysis of phase two tests for evaluating fenretinide for the treatment of GA related to AMD.

From the above, application of a medicament having an action to decrease blood RBP4 value (concentration) to the prophylaxis or treatment of ophthalmic diseases is expected. In the present specification, the "action to decrease blood RBP4 value (concentration)" is sometimes referred to as an "RBP4-lowering action", and the "medicament having an action to decrease blood RBP4 value (concentration)" is sometimes referred to as an "RBP4-lowering drug".

Patent document 2 discloses the following compound having a blood glucose lowering and glucose tolerance improving effect:

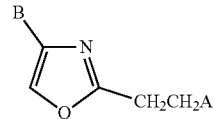

wherein each symbol is as defined in the document.

Patent document 3 discloses the following compound useful as a therapeutic agent for metabolic bone diseases:

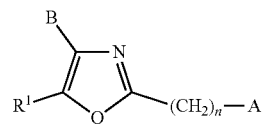

wherein each symbol is as defined in the document.

Patent document 4 discloses the following compound having an RBP4-lowering action and useful for the prophylaxis or treatment of diabetes, obesity and the like:

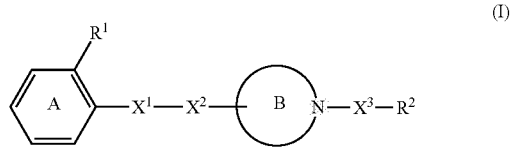

wherein each symbol is as defined in the document.

Patent document 5 discloses the following compound having an RBP4-lowering action and useful for the prophylaxis or treatment of diabetes and the like:

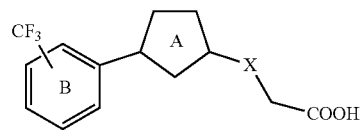

wherein each symbol is as defined in the document.

Patent document 6 discloses the following compound having an RBP4-lowering action and useful for the prophylaxis or treatment of diabetes, age-related macular degeneration and the like:

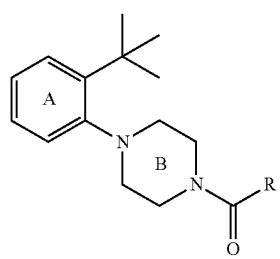

wherein each symbol is as defined in the document.

Patent document 7 discloses the following compound used for the analysis of a polypeptide sequence:

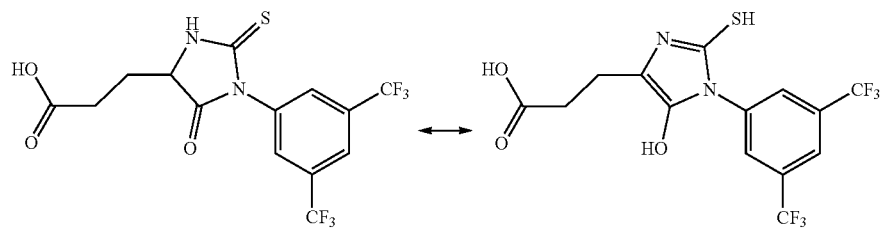 [SMILES: O=C(O)CCC1NC(=S)N(c2cc(C(F)(F)F)cc(C(F)(F)F)c2)C1=O ; O=C(O)CCc1nc(S)n(-c2cc(C(F)(F)F)cc(C(F)(F)F)c2)c1O]

Patent document 8 discloses the following compound having an RBP4-lowering action:

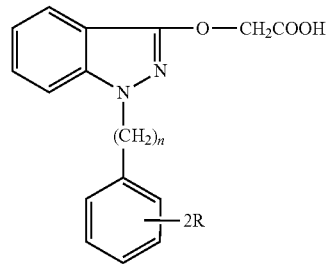

wherein each symbol is as defined in the document.

DOCUMENT LIST

Patent Documents patent document 1: WO 2009/042444
patent document 2: U.S. Pat. No. 5,239,080
patent document 3: U.S. Pat. No. 5,371,098
patent document 4: WO 2009/051244
patent document 5: WO 2009/145286
patent document 6: WO 2010/119992
patent document 7: WO 2003/031984
patent document 8: U.S. Pat. No. 3,625,970

Non-Patent Document non-patent document 1: Biochim. Biophys. Acta, 1294, 48-54 (1996)

SUMMARY OF THE INVENTION

Problems to be Solved by the Invention

An object of the present invention is to provide a heterocyclic compound having a RBP4-lowering action and useful for the prophylaxis or treatment of a disease or condition mediated by an increase in RBP4 or retinol supplied by RBP4 such as age-related macular degeneration, Stargardt's disease and the like, and a medicament containing same.

Means of Solving the Problems

The present inventors have conducted intensive studies in an attempt to solve the above-mentioned problems and found that a compound represented by the following formula (I) has a superior RBP4-lowering action, which resulted in the completion of the present invention.

Therefore, the present invention provides the following.
[1] A compound represented by the formula (I):

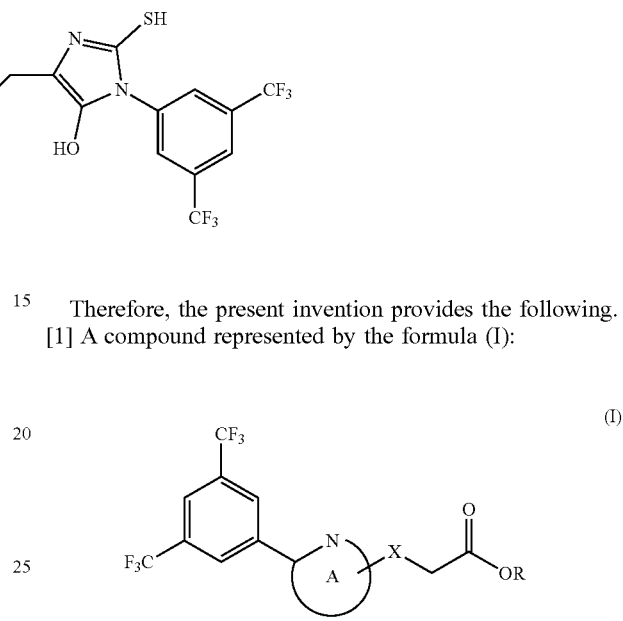

wherein
ring A is an optionally further substituted monocyclic nitrogen-containing aromatic heterocycle;
X is $CH_2$ or O; and
R is a hydrogen atom or a $C_{1-6}$ alkyl group, excluding
3-{4-[3,5-bis(trifluoromethyl)phenyl]-1,3-oxazol-2-yl}propanoic acid;
3-{4-[3,5-bis(trifluoromethyl)phenyl]-1,3-oxazol-2-yl}propanoic acid methyl ester;
3-{4-[3,5-bis(trifluoromethyl)phenyl]-1,3-oxazol-2-yl}propanoic acid ethyl ester; and
3-(3-(3,5-bis(trifluoromethyl)phenyl)-1,2,4-oxadiazol-5-yl)propanoic acid,
or a salt thereof (sometimes to be abbreviated as "compound (I)" in the present specification);
[2] the compound of the above-mentioned [1], wherein R is a hydrogen atom, or a salt thereof;
[3] the compound of the above-mentioned [1], wherein ring A is an optionally further substituted, monocyclic nitrogen-containing aromatic heterocycle free of a hetero atom other than nitrogen atom as a ring-constituting atom, or a salt thereof;
[4] the compound of the above-mentioned [1] or [2], wherein ring A is a pyrazole ring, a pyridine ring or a pyrimidine ring, or a salt thereof;
[5] ((2-(3,5-bis(trifluoromethyl)phenyl)pyrimidin-5-yl)oxy)acetic acid or a salt thereof;
[6] ((6-(3,5-bis(trifluoromethyl)phenyl)pyridin-3-yl)oxy)acetic acid or a salt thereof;
[7] 3-(3-(3,5-bis(trifluoromethyl)phenyl)-1H-pyrazol-1-yl)propanoic acid or a salt thereof;
[8] ((4-(3,5-bis(trifluoromethyl)phenyl)-1,3-oxazol-2-yl)oxy)acetic acid or a salt thereof;
[9] ((1-(3,5-bis(trifluoromethyl)phenyl)-1H-pyrazol-3-yl)oxy)acetic acid or a salt thereof;
[10] a medicament comprising the compound of [1] or [2] or a salt thereof;
[11] the medicament of [10], which is a retinol binding protein 4 lowering drug;

[12] the medicament of [10], which is a prophylactic or therapeutic agent for macular degeneration and/or Stargardt's disease;

[13] the compound of [1] or [2], or a salt thereof for use in the prophylaxis or treatment of macular degeneration and/or Stargardt's disease;

[14] a method of lowering retinol binding protein 4 in a mammal, comprising administering an effective amount of the compound of [1] or [2], or a salt thereof to the mammal;

[15] a method for the prophylaxis or treatment of macular degeneration and/or Stargardt's disease in a mammal, comprising administering an effective amount of the compound of [1] or [2], or a salt thereof to the mammal;

[16] use of the compound of [1] or [2], or a salt thereof in producing a prophylactic or therapeutic agent for macular degeneration and/or Stargardt's disease;

[17] the compound of [1], wherein when ring A is an optionally further substituted, monocyclic nitrogen-containing aromatic heterocycle free of a hetero atom other than nitrogen atom as a ring-constituting atom, X is $CH_2$ or O, and when ring A is an optionally further substituted, monocyclic nitrogen-containing aromatic heterocycle containing, as a ring-constituting atom, a hetero atom other than nitrogen atom, X is O, or a salt thereof.

Effect of the Invention

According to the present invention, a prophylactic or therapeutic agent for a disease or condition mediated by an increase in RBP4 or retinol supplied by RBP4 such as age-related macular degeneration, Stargardt's disease and the like is provided.

DETAILED DESCRIPTION OF THE INVENTION

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-20}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following substituent group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),

(51) a ($C_{1-6}$ alkyl) ($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, triazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and
8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and
9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include the "heterocyclic group" containing at least one nitrogen atom as a ring-constituting atom.

In the present specification, examples of the "optionally substituted heterocyclic group" include a heterocyclic group optionally having substituent(s) selected from the aforementioned substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxycarbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{16}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{716}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{16}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted amino group include an amino group, a mono- or di-(optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{614}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{16}$ alkyl-carbamoyl)amino group (e.g., methylcarbamoylamino), a (mono- or di-$C_{7-16}$ aralkyl-carbamoyl)amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl)amino group (e.g., N-acetyl-N-methylamino) and a ($C_{1-6}$ alkyl) ($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocycloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, triazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxazine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepanine, diazepane, azepine, azocane, diazocane, oxepane and the like; and
9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include the "heterocycle" containing at least one nitrogen atom as a ring-constituting atom.

In the present specification, the "monocyclic nitrogen-containing aromatic heterocycle" of the "optionally further substituted monocyclic nitrogen-containing aromatic heterocycle" is, for example, the above-mentioned "aromatic heterocycle" which is monocyclic and contains, as a ring-constituting atom, at least one nitrogen atom, and the substituent therefor includes the above-mentioned "substituent".

Each symbol in the formula (I) is defined in detail below.

Ring A shows an optionally further substituted monocyclic nitrogen-containing aromatic heterocycle. In the formula (I), the atom on ring A to which a group represented by

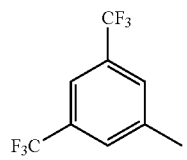

is bonded is not limited to a carbon atom, and may be a hetero atom (e.g., nitrogen atom).

Examples of the "monocyclic nitrogen-containing aromatic heterocycle" of the "optionally further substituted monocyclic nitrogen-containing aromatic heterocycle" for ring A include a 5- or 6-membered monocyclic nitrogen-containing aromatic heterocycle (e.g., a pyrazole ring, an oxazole ring, a pyridine ring, a pyrimidine ring).

The "monocyclic nitrogen-containing aromatic heterocycle" of the "optionally further substituted monocyclic nitrogen-containing aromatic heterocycle" for ring A is optionally further substituted at substitutable position(s) by 1 to 3 (preferably 1 or 2) substituents other than 3,5-bis(trifluoromethyl)phenyl group and HOOC—CH$_2$—X— group.

Examples of the "substituent" include halogen atom (e.g., fluorine, chlorine, bromine, iodine), optionally halogenated C$_{1-6}$ alkyl group (e.g., trifluoromethyl), C$_{3-6}$ cycloalkyl group, C$_{1-6}$ alkoxy group, and C$_{6-14}$ aryl group (e.g., phenyl).

As ring A, a monocyclic nitrogen-containing aromatic heterocycle which is not further substituted, namely, a monocyclic nitrogen-containing aromatic heterocycle not substituted by a substituent other than a 3,5-bis(trifluoromethyl)phenyl group and a HOOC—CH$_2$—X— group is preferable. In the present specification, the "monocyclic nitrogen-containing aromatic heterocycle which is not further substituted (not substituted by a substituent other than 3,5-bis(trifluoromethyl)phenyl group and HOOC—CH$_2$—X— group)" for ring A is sometimes abbreviated simply as "monocyclic nitrogen-containing aromatic heterocycle".

In another embodiment of the present invention, ring A is preferably an optionally further substituted, monocyclic nitrogen-containing aromatic heterocycle (e.g., a pyrazole ring, a pyridine ring, a pyrimidine ring) free of a hetero atom other than nitrogen atom as a ring-constituting atom, more preferably, a pyrazole ring, a pyridine ring or a pyrimidine ring.

X is CH$_2$ or O.

R is a hydrogen atom or a C$_{1-6}$ alkyl group.

Examples of the "C$_{1-6}$ alkyl group" for R include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

R is preferably a hydrogen atom.

In a preferable embodiment of the present invention, when ring A is an optionally further substituted, monocyclic nitrogen-containing aromatic heterocycle (e.g., a pyrazole ring, a pyridine ring, a pyrimidine ring) free of a hetero atom other than nitrogen atom as a ring-constituting atom, X is CH$_2$ or O, and when ring A is an optionally further substituted, monocyclic nitrogen-containing aromatic heterocycle (e.g., an oxazole ring) containing, as a ring-constituting atom, a hetero atom other than nitrogen atom, X is O.

Preferable examples of compound (I) include the following compounds.

Compound I-1

Compound (I) wherein ring A is an optionally further substituted 5- or 6-membered monocyclic nitrogen-containing aromatic heterocycle (e.g., a pyrazole ring, an oxazole ring, a pyridine ring, a pyrimidine ring);
X is CH$_2$ or O; and
R is a hydrogen atom or a C$_{1-6}$ alkyl group (e.g., methyl, ethyl).

Compound 1-2

Compound (I) wherein ring A is a 5- or 6-membered monocyclic nitrogen-containing aromatic heterocycle (e.g., a pyrazole ring, an oxazole ring, a pyridine ring, a pyrimidine ring);

X is $CH_2$ or O; and R is a hydrogen atom or a $C_{1-6}$ alkyl group (e.g., methyl, ethyl).

Compound 1-3

Compound (I) wherein ring A is a pyrazole ring, an oxazole ring, a pyridine ring or a pyrimidine ring;
X is $CH_2$ or O; and
R is a hydrogen atom or a $C_{1-6}$ alkyl group (e.g., methyl, ethyl).

Compound 1-4

Compound (I) wherein ring A is an optionally further substituted, monocyclic nitrogen-containing aromatic heterocycle (e.g., a pyrazole ring, a pyridine ring, a pyrimidine ring) free of a hetero atom other than nitrogen atom as a ring-constituting atom;
X is $CH_2$ or O; and
R is a hydrogen atom or a $C_{1-6}$ alkyl group (e.g., methyl, ethyl).

Compound 1-5

Compound (I) wherein ring A is monocyclic nitrogen-containing aromatic heterocycle (e.g., a pyrazole ring, a pyridine ring, a pyrimidine ring) free of a hetero atom other than nitrogen atom as a ring-constituting atom;
X is $CH_2$ or O; and
R is a hydrogen atom or a $C_{1-6}$ alkyl group (e.g., methyl, ethyl).

Compound 1-6

Compound (I) wherein ring A is a pyrazole ring, a pyridine ring or a pyrimidine ring;
X is $CH_2$ or O; and
R is a hydrogen atom or a $C_{1-6}$ alkyl group (e.g., methyl, ethyl).

Compound 1-7

Compound (I) wherein ring A is a pyrazole ring, a pyridine ring or a pyrimidine ring;
X is $CH_2$ or O; and
R is a hydrogen atom.

Specific examples of compound (I) include the compounds of Examples 1 to 10. Of these, more preferred are the compounds of Examples 1 to 5.

When compound (I) is a salt, examples thereof include metal salts, ammonium salts, salts with organic bases, salts with inorganic acids, salts with organic acids, salts with basic or acidic amino acids. As preferable examples of the metal salt, alkali metal salts such as sodium salt, potassium salt and the like; alkaline earth metal salts such as calcium salt, magnesium salt, barium salt and the like; aluminum salt can be mentioned. As preferable examples of the salts with organic bases, salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like can be mentioned. As preferable examples of the salts with inorganic acids, salts with hydrochloric acid, hydrobromic acid, nitric acid, sulfuric acid, phosphoric acid and the like can be mentioned. As preferable examples of the salts with organic acids, salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like can be mentioned. As preferable examples of the salts with basic amino acids, salts with arginine, lysine, ornithine and the like can be mentioned. As preferable examples of the salts with acidic amino acids, salts with aspartic acid, glutamic acid and the like can be mentioned.

Of these, pharmaceutically acceptable salts are preferable. For example, when a compound has an acidic functional group therein, inorganic salts such as alkali metal salts (e.g., sodium salt, potassium salt and the like), alkaline earth metal salts (e.g., calcium salt, magnesium salt, and the like) and the like, ammonium salt and the like can be mentioned. When a compound has a basic functional group therein, salts with inorganic acids such as hydrochloric acid, hydrobromic acid, nitric acid, sulfuric acid, phosphoric acid and the like, and salts with organic acids such as acetic acid, phthalic acid, fumaric acid, oxalic acid, tartaric acid, maleic acid, citric acid, succinic acid, methanesulfonic acid, benzenesulfonic acid, p-toluenesulfonic acid and the like can be mentioned.

In the present specification, compound (I), crystal of compound (I), prodrug of compound (I) and the like are sometimes collectively abbreviated as "the compound of the present invention".

Production Method

The production method of the compound of the present invention is explained in the following.

The starting materials and reagents used in each step in the following production method, and the obtained compounds each may form a salt. Examples of the salt include those similar to the aforementioned salts of the compound of the present invention and the like.

When the compound obtained in each step is a free compound, it can be converted to a desired salt by a method known per se. Conversely, when the compound obtained in each step is a salt, it can be converted to a free form or a desired other kind of salt by a method known per se.

The compound obtained in each step can also be used for the next reaction as a reaction mixture thereof or after obtaining a crude product thereof. Alternatively, the compound obtained in each step can be isolated and/or purified from the reaction mixture by a separation means such as concentration, crystallization, recrystallization, distillation, solvent extraction, fractionation, chromatography and the like according to a conventional method.

When the starting materials and reagent compounds of each step are commercially available, the commercially available products can be used as they are.

In the reaction of each step, while the reaction time varies depending on the reagents and solvents to be used, unless otherwise specified, it is generally 1 min to 48 hr, preferably 10 min to 8 hr.

In the reaction of each step, while the reaction temperature varies depending on the reagents and solvents to be used, unless otherwise specified, it is generally −78° C. to 300° C., preferably −78° C. to 150° C.

In the reaction of each step, while the pressure varies depending on the reagents and solvents to be used, unless otherwise specified, it is generally 1 atm to 20 atm, preferably 1 atm to 3 atm.

In the reaction of each step, for example, microwave synthesizers such as Initiator manufactured by Biotage and the like are sometimes used. While the reaction temperature varies depending on the reagents and solvents to be used, unless otherwise specified, it is generally room temperature to 300° C., preferably 50° C. to 250° C. While the reaction time varies depending on the reagents and solvents to be used, unless otherwise specified, it is generally 1 min to 48 hr, preferably 1 min to 8 hr.

In the reaction of each step, unless otherwise specified, a reagent is used in 0.5 equivalent to 20 equivalents, preferably 0.8 equivalent to 5 equivalents, relative to the substrate. When a reagent is used as a catalyst, the reagent is used in 0.001 equivalent to 1 equivalent, preferably 0.01 equivalent to 0.2 equivalent, relative to the substrate. When the reagent is also a reaction solvent, the reagent is used in a solvent amount.

In the reaction of each step, unless otherwise specified, it is performed without solvent or by dissolving or suspending in a suitable solvent. Specific examples of the solvent include those described in Examples and the following.
alcohols: methanol, ethanol, tert-butyl alcohol, 2-methoxyethanol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane and the like;
amides: N,N-dimethylformamide, N-methylpyrrolidone and the like;
halogenated hydrocarbons: dichloromethane, carbon tetrachloride and the like;
nitriles: acetonitrile and the like;
sulfoxides: dimethyl sulfoxide and the like;
aromatic organic bases: pyridine and the like;
acid anhydrides: acetic anhydride and the like;
organic acids: formic acid, acetic acid, trifluoroacetic acid and the like;
inorganic acids: hydrochloric acid, sulfuric acid and the like;
esters: ethyl acetate and the like;
ketones: acetone, methyl ethyl ketone and the like; and
water.

Two or more kinds of the above-mentioned solvents may be used by mixing at an appropriate ratio.

When a base is used in the reaction of each step, for example, bases shown below or those described in Examples are used.
inorganic bases: sodium hydroxide, magnesium hydroxide and the like;
basic salts: sodium carbonate, calcium carbonate, sodium hydrogen carbonate, potassium carbonate, potassium phosphate, cesium carbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;
metal alkoxides: sodium ethoxide, potassium tert-butoxide and the like;
alkali metal hydrides: sodium hydride and the like;
metal amides: sodium amide, lithium diisopropyl amide, lithium hexamethyl disilazide and the like; and
organic lithiums: n-butyllithium and the like.

When an acid or acidic catalyst is used in the reaction of each step, for example, acids and acidic catalysts shown below or those described in Examples are used.
inorganic acids: hydrochloric acid, sulfuric acid, nitric acid, hydrobromic acid, phosphoric acid and the like;
organic acids: acetic acid, trifluoroacetic acid, citric acid, p-toluenesulfonic acid, 10-camphorsulfonic acid and the like; and Lewis acids: boron trifluoride diethyl ether complex, zinc iodide, anhydrous aluminum chloride, anhydrous zinc chloride, anhydrous iron chloride and the like.

Unless otherwise specified, the reaction of each step is performed according to a method known per se, for example, the methods described in Jikken Kagaku Kouza 5th edition, vol. 13-vol. 19 (The Chemical Society of Japan ed.); Shinjikken Kagaku Kouza (Courses in Experimental Chemistry), vol. 14-vol. 15 (The Chemical Society of Japan ed.); Fine Organic Chemistry rev. 2nd edition (L. F. Tietze, Th. Eicher, NANKODO); rev. Organic Name Reactions, Their Mechanism and Essence (Hideo Togo, Kodansha); ORGANIC SYNTHESES Collective Volume I-VII (John Wiley & Sons Inc); Modern Organic Synthesis in the Laboratory, A Collection of Standard Experimental Procedures (Jie Jack Li, OXFORD UNIVERSITY); Comprehensive Heterocyclic Chemistry III, Vol. 1-Vol. 14 (Elsevier Japan KK); Strategic Applications of Named Reactions in Organic Synthesis (translation supervisor Kiyoshi Tomioka, KAGAKUDOJIN); Comprehensive Organic Transformations (VCH Publishers Inc.), 1989 and the like, or the methods described in the Examples.

In each step, protection or deprotection of a functional group is performed by the method known per se, for example, the methods described in "Protective Groups in Organic Synthesis, 4th Ed." (Theodora W. Greene, Peter G. M. Wuts) Wiley-Interscience, 2007; "Protecting Groups 3rd Ed." (P. J. Kocienski) Thieme, 2004 and the like, or the methods described in the Examples.

Examples of the protecting group of the hydroxyl group of alcohol and the like and a phenolic hydroxyl group include ether protecting groups such as methoxymethyl ether, benzyl ether, t-butyldimethylsilyl ether, tetrahydropyranyl ether and the like; carboxylate protecting groups such as acetate and the like; sulfonate ester protecting groups such as methanesulfonate ester and the like; carbonate ester protecting groups such as t-butylcarbonate and the like, and the like.

Examples of the protecting group of the carbonyl group of aldehyde include acetal protecting groups such as dimethyl acetal and the like; cyclic acetal protecting groups such as cyclic 1,3-dioxane and the like, and the like.

Examples of the protecting group of the carbonyl group of ketone include ketal protecting groups such as dimethyl ketal and the like; cyclic ketal protecting groups such as cyclic 1,3-dioxane and the like; oxime protecting groups such as O-methyloxime and the like; hydrazone protecting groups such as N,N-dimethylhydrazone and the like, and the like.

Examples of the carboxyl protecting group include ester protecting groups such as methyl ester and the like; amide protecting groups such as N,N-dimethylamide and the like, and the like.

Examples of the thiol protecting group include ether protecting groups such as benzyl thioether and the like; ester protecting groups such as thioacetate ester, thiocarbonate, thiocarbamate and the like, and the like.

Examples of the protecting group of an amino group and an aromatic hetero ring such as imidazole, pyrrole, indole and the like include carbamate protecting groups such as benzyl carbamate and the like; amide protecting groups such as acetamide and the like; alkylamine protecting groups such as N-triphenylmethylamine and the like, sulfonamide protecting groups such as methanesulfonamide and the like, and the like.

The protecting group can be removed by a method known per se, for example, a method using acid, base, ultraviolet light, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide), a reduction method and the like.

When a reduction reaction is performed in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane tetrahydrofuran complex and the like; Raney nickel; Raney cobalt; hydrogen; formic acid; triethylsilane and the like. When a carbon-carbon double bond or triple bond is reduced, a method using a catalyst such as palladium-carbon, Lindlar catalyst and the like.

When an oxidation reaction is performed in each step, examples of an oxidant to be used include peracids such as m-chloroperbenzoic acid (mCPBA), hydrogen peroxide, t-butyl hydroperoxide and the like; perchlorates such as tetrabutylammonium perchlorate and the like; chlorates such as sodium chlorate and the like; chlorites such as sodium chlorite and the like; periodic acids such as sodium periodate and the like; high valent iodine reagents such as iodosylbenzene and the like; reagents containing manganese such as manganese dioxide, potassium permanganate and the like; leads such as lead tetraacetate and the like; reagents containing chrome such as pyridinium chlorochromate (PCC), pyridinium dichromate (PDC), Jones reagent and the like; halogen compounds such as N-bromosuccinimide (NBS) and the like; oxygen; ozone; sulfur trioxide pyridine complex; osmium tetraoxide; selenium dioxide; 2,3-dichloro-5, 6-dicyano-1,4-benzoquinone (DDQ) and the like.

When a radical cyclization reaction is performed in each step, examples of the radical initiator to be used include azo compounds such as azobisisobutyronitrile (AIBN) and the like; water-soluble radical initiators such as 4,4'-azobis-4-cyanopentanoic acid (ACPA) and the like; triethylboron in the presence of air or oxygen; benzoyl peroxide and the like. In addition, examples of the radical reaction agent to be used include tributylstannane, tristrimethylsilylsilane, 1,1,2,2-tetraphenyldisilane, diphenylsilane, samarium iodide and the like.

When the Wittig reaction is performed in each step, examples of the Wittig reagent to be used include alkylidenephosphoranes and the like. Alkylidenephosphoranes can be prepared by a method known per se, for example, by reacting a phosphonium salt with a strong base.

When the Horner-Emmons reaction is performed in each step, examples of the reagent to be used include phosphonoacetic acid esters such as methyl dimethylphosphonoacetate, ethyl diethylphosphonoacetate and the like; and bases such as alkali metal hydrides, organic lithiums and the like.

When the Friedel-Crafts reaction is performed in each step, examples of the reagent to be used include a combination of Lewis acid and acid chloride or a combination of Lewis acid and alkylating agents (e.g., alkyl halides, alcohol, olefins and the like). Alternatively, an organic acid and an inorganic acid can also be used instead of the Lewis acid, and acid anhydride such as acetic anhydride and the like can also be used instead of acid chloride.

When an aromatic nucleophilic substitution reaction is performed in each step, a nucleophilic agent (e.g., amines, imidazole and the like) and a base (e.g., basic salts, organic bases and the like) are used as the reagent.

When a nucleophilic addition reaction with carbanion, a nucleophilic 1,4-addition reaction with carbanion (Michael addition reaction) or a nucleophilic substitution reaction with carbanion is performed in each step, examples of the base to be used for developing carbanion include organic lithiums, metal alkoxides, inorganic bases, organic bases and the like.

When the Grignard reaction is performed in each step, examples of the Grignard reagent include aryl magnesium halides such as phenyl magnesium bromide and the like; and alkyl magnesium halides such as methyl magnesium bromide and the like. The Grignard reagent can be prepared by a method known per se, for example, by reacting alkyl halide or aryl halide with metal magnesium in ether or tetrahydrofuran as a solvent.

When the Knoevenagel condensation reaction is performed in each step, an active methylene compound held between two electron-withdrawing groups (e.g., malonic acid, diethyl malonate, malononitrile and the like) and a base (e.g., organic bases, metal alkoxides, inorganic bases) are used as the reagents.

When the Vilsmeier-Haack reaction is performed in each step, phosphoryl chloride and an amide derivative (e.g., N,N-dimethylformamide and the like) are used as the reagents.

When an azidation reaction of alcohols, alkylhalides or sulfonate esters is performed in each step, examples of the azidation agent to be used include diphenylphosphoryl azide (DPPA), trimethylsilylazide, sodium azide and the like. For example, when alcohols are azidated, a method using diphenylphosphoryl azide and 1,8-diazabicyclo[5,4,0]undec-7-ene (DBU), a method using trimethylsilylazide and the Lewis acid and the like can be employed.

When a reductive amination reaction is performed in each step, examples of the reducing agent to be used include sodium triacetoxyborohydride, sodium cyanoborohydride, hydrogen, formic acid and the like. When the substrate is an amine compound, examples of the carbonyl compound to be used besides para-formaldehyde include aldehydes such as acetaldehyde and the like, ketones such as cyclohexanone and the like. When the substrate is a carbonyl compound, examples of the amines to be used include ammonia, primary amines such as methylamine and the like; secondary amines such as dimethylamine and the like, and the like.

When the Mitsunobu reaction is performed in each step, azodicarboxylate esters (e.g., diethyl azodicarboxylate (DEAD), diisopropyl azodicarboxylate (DIAD) and the like) and triphenylphosphine are used as the reagents.

When an esterification reaction, amidation reaction or ureation reaction is performed in each step, examples of the reagent to be used include halogenated acyl forms such as acid chloride, acid bromide and the like; and activated carboxylic acids such as acid anhydride, active ester form, sulfuric acid ester form and the like. Examples of the carboxylic acid activator include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride-n-hydrate (DMT-MM) and the like; carbonate ester condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methylpyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphate (HATU); sulfuric acid; a combination thereof and the like. When a carbodiimide condensing agent is used, additives such as 1-hydroxybenzotriazole (HOBt), N-hydroxysuccinimide (HOSu), dimethylaminopyridine (DMAP) and the like can be further added to the reaction.

When a coupling reaction is performed in each step, examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride, palladium(II) acetate and the like; nickel compounds such as tetrakis(triphenylphosphine)nickel(0) and the like; rhodium compounds such as tris(triphenylphosphine)rhodium(III) chloride and the like; a cobalt compound; copper compounds such as copper oxide, copper(I) iodide and the like; a platinum compound and the like. A base may be further added to the reaction and examples of such base include inorganic bases, basic salts and the like.

When a thiocarbonylation reaction is performed in each step, diphosphorus pentasulfide is representatively used as a thiocarbonylating agent. Besides diphosphorus pentasulfide, a reagent having a 1,3,2,4-dithiadiphosphetane-2,4-disulfide structure such as 2,4-bis(4-methoxyphenyl-1,3,2,4-dithiadiphosphetane-2,4-disulfide (Lawesson reagent) and the like may also be used.

When the Wohl-Ziegler reaction is performed in each step, examples of the halogenating agent to be used include N-iodosuccinimide, N-bromosuccinimide (NBS), N-chlorosuccinimide (NCS), bromine, sulfuryl chloride and the like. Furthermore, the reaction can be accelerated by adding heat, light, radical initiators such as benzoyl peroxide, azobisisobutyronitrile and the like to the reaction.

When a halogenating reaction of a hydroxy group is performed in each step, examples of the halogenating agent to be used include acid halide of hydrohalic acid and inorganic acid; specifically, hydrochloric acid, thionyl chloride, phosphorus oxychloride and the like for chlorination, and 48% hydrobromic acid and the like for bromination. In addition, a method of obtaining a halogenated alkyl form from alcohol by reacting with triphenylphosphine and carbon tetrachloride or carbon tetrabromide, and the like may be used. Alternatively, a method of synthesizing a halogenated alkyl form via a two-step reaction including conversion of alcohol to sulfonic acid ester, and reacting same with lithium bromide, lithium chloride or sodium iodide may also be used.

When the Arbuzov reaction is performed in each step, examples of the reagent to be used include alkyl halides such as ethyl bromoacetate and the like; and phosphites such as triethyl phosphite, tri(isopropyl)phosphite and the like.

When a sulfonation reaction is performed in each step, examples of the sulfonylating agent to be used include methanesulfonyl chloride, p-toluenesulfonyl chloride, methanesulfonic anhydride, p-toluenesulfonic anhydride and the like.

When hydrolysis is performed in each step, an acid or a base is used as the reagent. In addition, when acid hydrolysis of t-butyl ester is performed, formic acid, triethylsilane and the like are sometimes added to reductively trap the by-produced t-butyl cation.

When a dehydrating reaction is performed in each step, examples of the dehydrating agent to be used include sulfuric acid, phosphorus pentaoxide, phosphorus oxychloride, N,N'-dicyclohexylcarbodiimide, alumina, polyphosphoric acid and the like.

When nitration reaction is performed in each step, examples of the nitrating agent to be used include nitric acid, fuming nitric acid, and copper nitrate. The reaction is activated by concentrated sulfuric acid, acetic anhydride and the like.

When halogenation reaction is performed in each step, examples of the halogenating agent to be used include N-iodosuccinimide, N-bromosuccinimide (NBS), N-chlorosuccinimide (NCS), iodine monochloride, iodine, bromine, sulfuryl chloride and the like can be mentioned. In this reaction, an additive such as trifluoroacetic acid and the like may be used for the activation of a halogenating agent.

When acylation reaction is performed in each step, amidation reaction, ureation reaction, carbamation reaction, thiocarbamation reaction and the like are performed. When carbamation reaction or thiocarbamation reaction is performed, examples of the reagent to be used include triphosgene, carbonate condensing agents such as 1,1-carbonyldiimidazole (CDI) and the like, chlorocarbonates, chlorocarbonic acid thio esters, isothiocyanates and the like.

When cyclization reaction is performed in each step, it is performed by the Mitsunobu reaction or an alkylation reaction. When an alkylation reaction is performed, a base is used as the reagent.

Compound (4) can be produced from compound (1) by the method shown in scheme 1 or a method analogous thereto or the method described in the Examples. In the formula, $R^1$ shows an optionally substituted hydrocarbon group.

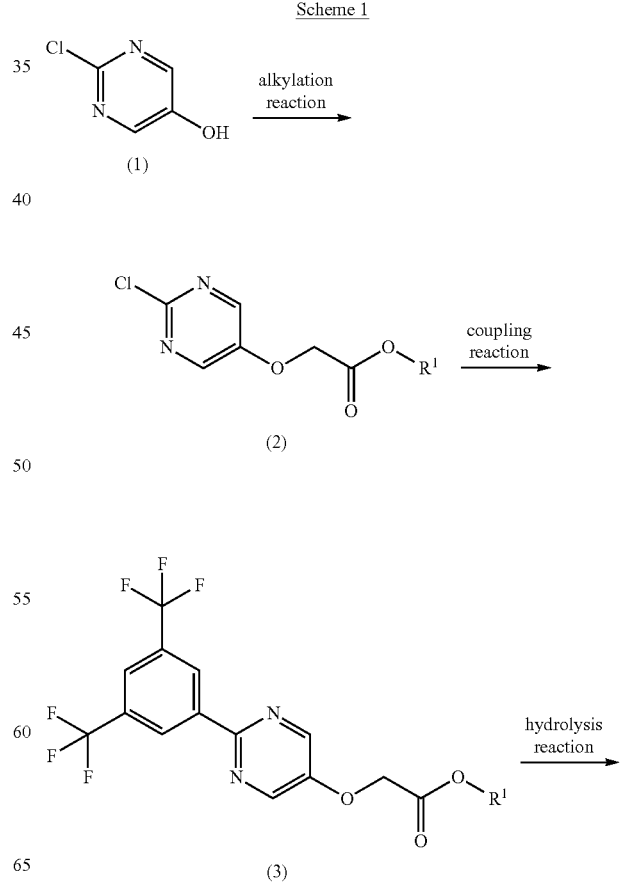

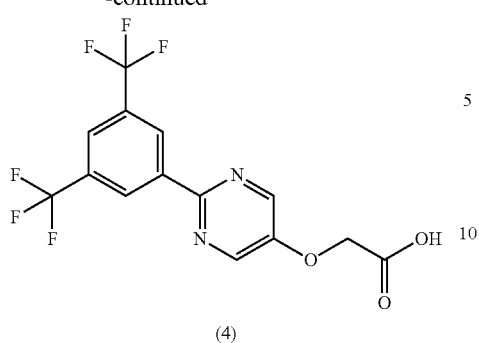

(4)

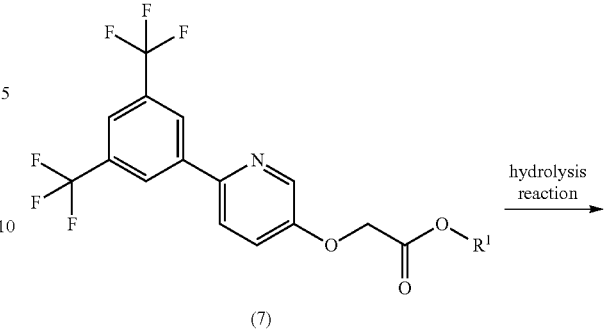

(7)

Compound (2) can be produced by an alkylation reaction of compound (1), tert-butyl 2-bromoacetate and a base. Examples of the solvent to be used include N,N-dimethylformamide and the like.

A commercially available product may be directly used as compound (1), or compound (1) can be produced by a method known per se or a method analogous thereto.

Compound (3) can be produced by a coupling reaction of compound (2), (3,5-bis(trifluoromethyl)phenyl)boronic acid, palladium catalyst and a base. Examples of the palladium catalyst to be used include tetrakis(triphenylphosphine)palladium (0) and the like, and examples of the solvent include 1,2-dimethoxyethane and water and the like.

Compound (4) can be produced by hydrolysis of compound (3) and trifluoroacetic acid.

Compound (8) can be produced from compound (5) by the method shown in scheme 2 or a method analogous thereto or the method described in the Examples. In the formula, $R^1$ shows an optionally substituted hydrocarbon group.

Scheme 2

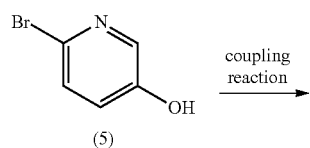

(5)

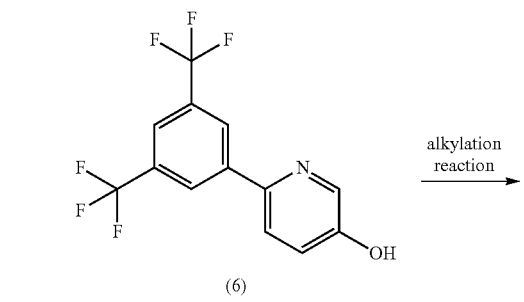

(6)

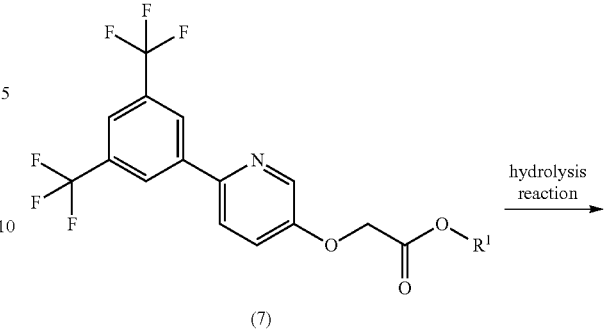

(8)

Compound (6) can be produced by a coupling reaction of compound (5), (3,5-bis(trifluoromethyl)phenyl)boronic acid, a palladium catalyst and a base. Examples of the palladium catalyst to be used include tetrakis(triphenylphosphine)palladium (0) and the like, and examples of the solvent include 1,2-dimethoxyethane, water and the like.

A commercially available product may be directly used as compound (5), or compound (5) can be produced by a method known per se or a method analogous thereto.

Compound (7) can be produced by an alkylation reaction of compound (6), tert-butyl 2-bromoacetate and a base. Examples of the solvent to be used include N,N-dimethylformamide and the like.

Compound (8) can be produced by hydrolysis of compound (7) and a base. Examples of the solvent to be used include water, ethanol, tetrahydrofuran and the like.

Compound (13) can be produced from compound (9) by the method shown in scheme 3 or a method analogous thereto or the method described in the Examples.

Scheme 3

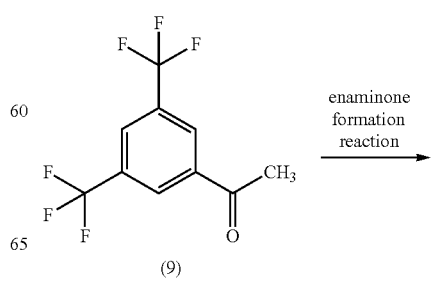

(9)

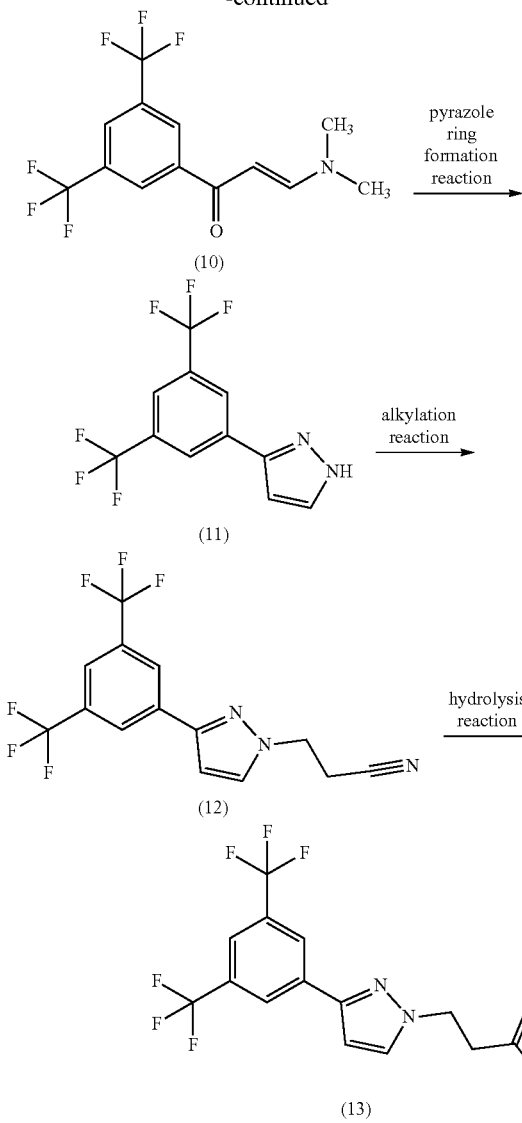

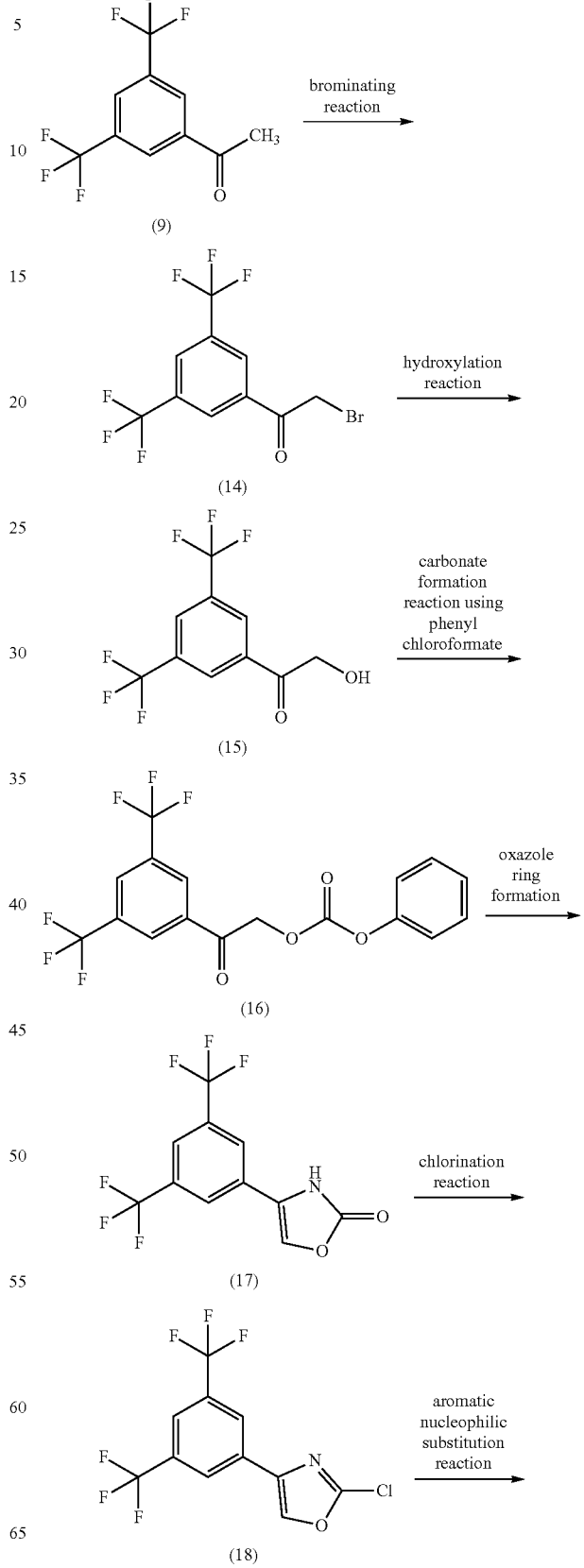

Scheme 4

Compound (10) can be produced by an enaminone formation reaction of compound (9) and N,N-dimethylformamide dimethyl acetal.

A commercially available product may be directly used as compound (9), or compound (9) can be produced by a method known per se or a method analogous thereto.

Compound (11) can be produced by a pyrazole ring formation reaction of compound (10) and hydrazine monohydrate. Examples of the solvent to be used include acetic acid and the like.

Compound (12) can be produced by an alkylation reaction of compound (11), 3-bromopropionitrile and a base. Examples of the solvent to be used include N,N-dimethylformamide and the like.

Compound (13) can be produced by hydrolysis of compound (12) and hydrochloric acid. Examples of the solvent to be used include water and the like.

Compound (20) can be produced from compound (9) by the method shown in scheme 4 or a method analogous thereto or the method described in the Examples. In the formula, $R^1$ shows an optionally substituted hydrocarbon group.

-continued

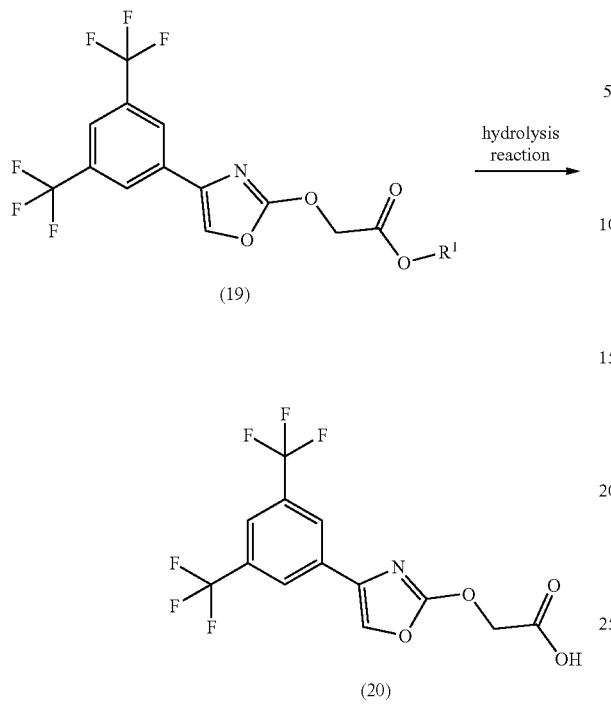

(19)

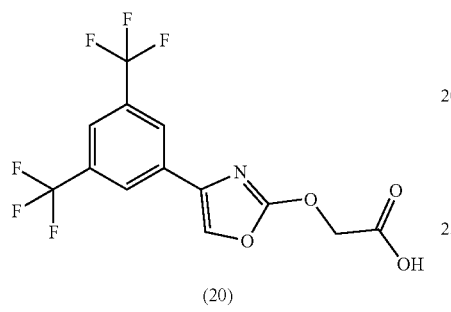

(20)

Compound (14) can be produced by a brominating reaction of compound (9) and bromine. Examples of the solvent to be used include acetic acid and the like.

Compound (15) can be produced by a hydroxylation reaction of compound (14) and sodium formate. Examples of the solvent to be used include methanol and the like.

Compound (16) can be produced by a carbonate formation reaction of compound (15), phenyl chloroformate and a base. Examples of the base to be used include pyridine and the like, and examples of the solvent include tetrahydrofuran and the like.

Compound (17) can be produced by an oxazole ring formation reaction of compound (16) and ammonium acetate. Examples of the solvent to be used include acetic acid and the like.

Compound (18) can be produced by a chlorination reaction of compound (17), phosphoryl chloride and N,N-diethylaniline.

Compound (19) can be produced by an aromatic nucleophilic substitution reaction of compound (18), tert-butyl 2-hydroxyacetate and sodium hydride. Examples of the solvent to be used include tetrahydrofuran and the like.

Compound (20) can be produced by hydrolysis of compound (19) and a base. Examples of the solvent to be used include water, methanol, tetrahydrofuran and the like.

Compound (25) can be produced from compound (21) by the method shown in scheme 5 or a method analogous thereto or the method described in the Examples. In the formula, $R^1$ shows an optionally substituted hydrocarbon group.

Scheme 5

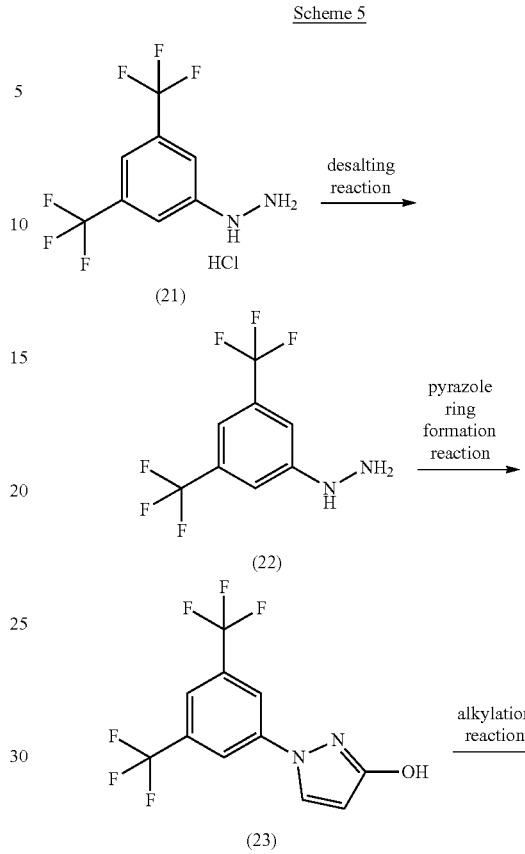

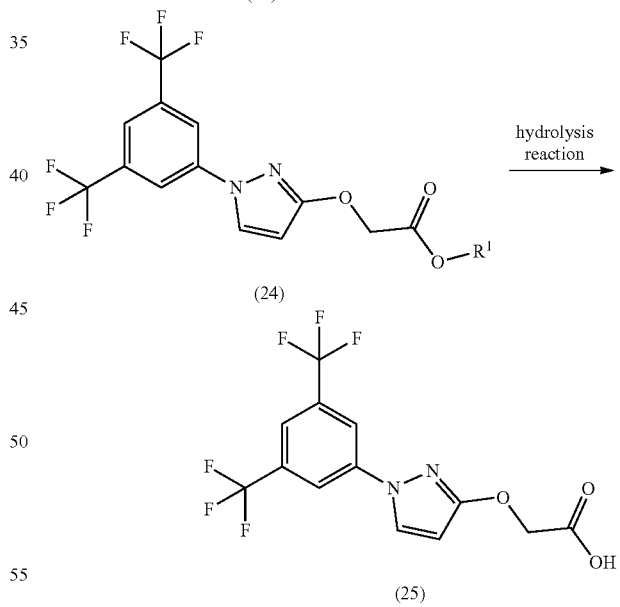

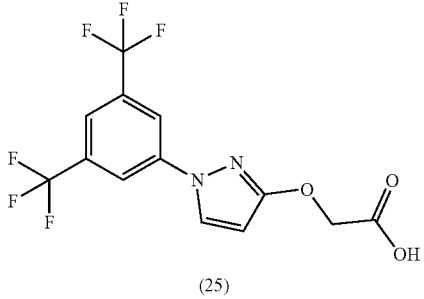

(25)

Compound (22) can be produced by a desalting reaction of compound (21) and sodium hydroxide. Examples of the solvent to be used include water, ethyl acetate and the like.

A commercially available product may be directly used as compound (21), or compound (21) can be produced by a method known per se or a method analogous thereto.

Compound (23) can be produced by a pyrazole ring formation reaction of compound (22), ethyl propiolate and a base. Examples of the solvent to be used include tert-butanol and the like.

Compound (24) can be produced by an alkylation reaction of compound (23), tert-butyl 2-bromoacetate and a base. Examples of the solvent to be used include N,N-dimethylformamide and the like.

Compound (25) can be produced by hydrolysis of compound (24) and a base. Examples of the solvent to be used include water, methanol, tetrahydrofuran and the like.

When compound (I) contains optical isomer, stereoisomer, positional isomer, or rotamer, these are also encompassed in compound (I), and can be obtained as a single product by synthesis methods and separation methods (e.g., concentration, solvent extraction, column chromatography, recrystallization etc.) known per se. For example, when compound (I) contains an optical isomer, an optical isomer resolved from the compound is also encompassed in compound (I).

An optical isomer can be produced by a method known per se. To be specific, an optical isomer is obtained using an optically active synthetic intermediate, or by optical resolution of a racemate of the final product by a conventional method.

The method of optical resolution may be a method known per se, such as a fractional recrystallization method, a chiral column method, a diastereomer method etc.

Compound (I) may be a crystal.

The crystal of compound (I) can be produced by crystallization of compound (I) by applying a crystallization method known per se.

Examples of the crystallization method include a method of crystallization from a solution, a method of crystallization from vapor, and a method of crystallization from a molten form.

As the analysis method of the obtained crystal, a crystal analysis method by powder X-ray diffraction is general. Furthermore, as a method of determining the crystal orientation, a mechanical method, an optical method and the like can also be mentioned.

The crystal of compound (I) obtained by the above-mentioned production method has high purity, high quality, and low hygroscopicity, is not denatured even after preservation under general conditions for a long term, and is extremely superior in stability. It is also superior in biological properties (e.g., pharmacokinetics (absorption, distribution, metabolism, excretion), efficacy expression), and thus is extremely useful as a medicament.

A prodrug of compound (I) means a compound which is converted to the compound (I) with a reaction due to an enzyme, an gastric acid, etc. under the physiological condition in the living body, that is, a compound which is converted to the compound (I) with oxidation, reduction, hydrolysis, etc. according to an enzyme; a compound which is converted to the compound (I) by hydrolysis etc. due to gastric acid, etc. A prodrug for compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.); a compound obtained by subjecting a hydroxy group in compound (I) to an acylation, alkylation, phosphorylation or boration [e.g., a compound obtained by subjecting an hydroxy group in compound (I) to an acetylation, palmitoylation, propanoylation, pivaloylation, succinylation, fumarylation, alanylation, dimethylaminomethylcarbonylation, etc.]; a compound obtained by subjecting a carboxyl group in compound (I) to an esterification or amidation [e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation, etc.] and the like. Any of these compounds can be produced from compound (I) by a method known per se.

A prodrug for compound (I) may also be one which is converted to compound (I) under physiological conditions, such as those described in "Development of Pharmaceutical Product", Vol. 7, Design of Molecules, p. 163-198, Published by HIROKAWA SHOTEN (1990).

Compound (I) may be any of a hydrate, a non-hydrate, a solvate and a non-solvate.

Compound (I) also encompasses a compound labeled with an isotope (e.g., $^3$H, $^{14}$C, $^{35}$S, $^{125}$I etc.) and the like.

Compound (I) also encompasses a deuterium conversion form wherein $^1$H is converted to $^2$H(D).

Compound (I) also encompasses a tautomer.

Compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, stability etc.). The cocrystal and cocrystal salt can be produced by cocrystallization method known per se.

Compound (I) may also be used as a PET tracer.

The compound of the present invention has a superior retinol binding protein 4-lowering action. The compound of the present invention also has a superior retinol binding protein 4 binding inhibitory action (retinol binding protein 4-TTR (transthyretin) binding inhibitory action).

Therefore, the compound of the present invention is useful as a safe medicament based on these actions. For example, the medicament of the present invention containing the compound of the present invention can be used as a prophylactic or therapeutic agent for retinol binding protein 4 associated diseases in mammals (e.g., mouse, rat, hamster, rabbit, cat, dog, bovine, sheep, monkey, human etc.).

When used in the present specification, treatment also includes suppression of the progression of a disease or condition.

Specifically, the compound of the present invention can be used prophylactic or therapeutic agent for a disease or condition mediated by an increase in RBP4 or retinol supplied by RBP4, for example, macular degeneration (e.g., dry (atrophic or non-vascular) age-related macular degeneration, exudative (wet or neovascular) age-related macular degeneration), geographic atrophy and/or denaturation of photoreceptor, macular dystrophy and retinal dystrophy, retinopathy (e.g., diabetic retinopathy, retinopathy of prematurity), retinitis pigmentosa, retinal vein occlusion, retinal artery obstruction, glaucoma, or Stargardt's disease (Stargardt disease).

The compound of the present invention can also be used as an agent for the prophylaxis or treatment of obesity, hyperlipidemia (e.g., hypertriglyceridemia, hypercholesterolemia, high LDL-cholesterolemia, hypo HDL-cholesterolemia, postprandial hyperlipidemia), hypertension, cardiac failure, diabetic complications [e.g., neuropathy, nephropathy, retinopathy, diabetic cardiomyopathy, cataract, macroangiopathy, osteopenia, hyperosmolar diabetic coma, infections (e.g., respiratory infection, urinary tract infection, gastrointestinal infection, dermal soft tissue infections, inferior limb infection), diabetic gangrene, xerostomia, hypacusis, cerebrovascular disorder, peripheral blood circulation disorder], metabolic syndrome, sarcopenia and the like.

The compound of the present invention can also be used as an agent for the prophylaxis or treatment of, for example, osteoporosis, cachexia (e.g., cancerous cachexia, tuberculous cachexia, diabetic cachexia, hemopathic cachexia, endocrinopathic cachexia, infectious cachexia or cachexia induced by acquired immunodeficiency syndrome), fatty liver, polycystic ovary syndrome, renal disease (e.g., diabetic nephropathy, glomerulonephritis, glomerulosclerosis, nephrotic syndrome, hypertensive nephrosclerosis, end-stage renal disorder), muscular dystrophy, myocardial infarction, angina pectoris, cerebrovascular disorder (e.g., cerebral infarction, cerebral apoplexy), Alzheimer's disease, Parkinson's disease, anxiety, dementia, insulin resistance syndrome, syndrome X, hyperinsulinemia, perception disorder in hyperinsulinemia, tumor (e.g., leukemia, breast cancer, prostate cancer, skin cancer), irritable bowel syndrome, acute or chronic diarrhea, inflammatory disease (e.g., chlonic rheumatoid arthritis, spondylitis deformans, osteoarthritis, lumbago, gout, postoperative or post-traumatic inflammation, swelling, neuralgia, pharyngolaryngitis, bladder inflammation, hepatitis (including nonalcoholic steato-hepatitis), pneumonia, pancreatitis, enteritis, inflammatory bowel disease (including inflammatory colitis), ulcerative colitis, gastric mucosa injury (including gastric mucosa injury caused by aspirin)), small intestinal mucosa injury, malabsorption, testis dysfunction, visceral obesity syndrome, and sarcopenia.

The compound of the present invention can also be used as an agent for lowering the level of serum retinol, serum RBP (retinol binding protein) and/or serum TTR (transthyretin) and can also be used as, for example, a prophylactic or therapeutic agent for hyperretinolemia (excess serum retinol level).

The compound of the present invention can also be used for the secondary prevention or prevention of the progression of the above-mentioned various diseases (e.g., cardiovascular events such as myocardial infarction and the like).

The compound of the present invention can be directly used as the medicament of the present invention, or as a pharmaceutical composition formed by mixing with a pharmacologically acceptable carrier by a means known per se, which is generally used for a production method of a pharmaceutical preparation.

The medicament of the present invention can be safely administered orally or parenterally to mammals (e.g., human, monkey, bovine, horse, swine, mouse, rat, hamster, rabbit, cat, dog, sheep, goat etc.).

As a medicament containing the compound of the present invention, the compound of the present invention can be used alone or as a pharmaceutical composition mixed with pharmacologically acceptable carriers, according to a method known per se as a production method of a pharmaceutical preparation (e.g., methods described in the Japanese Pharmacopeia, etc.). A medicament containing the compound of the present invention can be safely administered in the form of, for example, tablet (including sugar-coated tablet, film-coated tablet, sublingual tablet, orally disintegrating tablet, buccal tablet and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, cream, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal and intratumor administrations, administration to the vicinity of tumor, and administration to the lesion).

The representative content of the compound of the present invention in the medicament of the present invention is about 0.01 wt % to about 100 wt %, of the whole medicament.

While the dose of the compound of the present invention varies depending on the subject of administration, administration route, target disease, symptom and the like, a single dose is generally about 0.01 to 100 mg/kg body weight, preferably 0.05 to mg/kg body weight, more preferably 0.1 to 10 mg/kg body weight, for oral administration to adult macular degeneration patients, and the dose is desirably administered in 1 to 3 times per day.

As the above-mentioned pharmacologically acceptable carrier, which may be used for the production of the medicament of the present invention, various organic or inorganic carrier substances conventionally used as a preparation material can be mentioned. For example, excipient, lubricant, binder and disintegrant for solid preparations; solvent, solubilizing agents, suspending agent, isotonic agent, and buffer and soothing agent for liquid preparations can be mentioned. Where necessary, conventional additives such as preservatives, antioxidants, colorants, sweetening agents, adsorbing agents, wetting agents and the like can be used appropriately in suitable amounts.

As the excipient, for example, lactose, sucrose, D-mannitol, starch, corn starch, crystalline cellulose, light anhydrous silicic acid can be mentioned.

As the lubricant, for example, magnesium stearate, calcium stearate, talc, colloidal silica can be mentioned.

As the binder, for example, crystalline cellulose, sucrose, D-mannitol, dextrin, hydroxypropylcellulose, hydroxypropylmethylcellulose, polyvinylpyrrolidone, starch, saccharose, gelatin, methylcellulose, carboxymethylcellulose sodium can be mentioned.

As the disintegrant, for example, starch, carboxymethylcellulose, carboxymethylcellulose calcium, carboxymethylstarch sodium, L-hydroxypropylcellulose can be mentioned.

As the solvent, for example, water for injection, alcohol, propylene glycol, macrogol, sesame oil, corn oil, olive oil can be mentioned.

As the solubilizing agents, for example, polyethylene glycol, propylene glycol, D-mannitol, benzyl benzoate, ethanol, trisaminomethane, cholesterol, triethanolamine, sodium carbonate, sodium citrate can be mentioned.

As the suspending agent, for example, surfactants such as stearyltriethanolamine, sodium lauryl sulfate, lauryl aminopropionate, lecithin, benzalkonium chloride, benzethonium chloride, glycerol monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like can be mentioned.

As the isotonic agent, for example, glucose, D-sorbitol, sodium chloride, glycerin, D-mannitol can be mentioned.

As the buffer, for example, buffers such as phosphates, acetates, carbonates, citrates and the like, can be mentioned.

As the soothing agent, for example, benzyl alcohol can be mentioned.

As the preservatives, for example, paraoxybenzoates, chlorobutanol, benzyl alcohol, phenylethyl alcohol, dehydroacetic acid, sorbic acid can be mentioned.

As the antioxidant, for example, sulfites, ascorbic acid, α-tocopherol can be mentioned.

As the colorant, for example, water-soluble edible tar pigments (e.g., foodcolors such as Food Color Red Nos. 2 and 3, Food Color Yellow Nos. 4 and 5, Food Color Blue Nos. 1 and 2 and the like), water insoluble lake pigments (e.g., aluminum salt of the aforementioned water-soluble edible tar pigment and the like), natural pigments (e.g., β-carotene, chlorophil, ferric oxide red etc.) can be mentioned.

As the sweetening agent, for example, saccharin sodium, dipotassium glycyrrhizinate, aspartame, stevia can be mentioned.

As the adsorbent, porous starch, calcium silicate (trade name: Florite RE), magnesium aluminometasilicate (trade name: Neusilin), light anhydrous silicic acid (trade name: Sylysia) can be mentioned.

As the wetting agent, propylene glycol monostearate, sorbitan monooleate, diethylene glycol monolaurate, polyoxyethylene lauryl ether can be mentioned.

When the present compound is used as an ointment, it is produced by mixing the present compound with a conventional ointment base at a concentration of about 0.001 to 3% (W/W), preferably about 0.01 to 1% (W/W). The production of ointment preferably includes a step of powderizing the present compound or a step of sterilizing the preparation. Ointment is administered 1 to 4 times per day according to the condition of the patients.

As the ointment base, purified lanolin, white petrolatum, macrogol, Plastibase, liquid paraffin can be mentioned.

With the aim of enhancing the action of the compound of the present invention or decreasing the dose of the compound and the like, the compound can be used in combination with medicaments such as therapeutic agents for diabetes, therapeutic agents for diabetic complications, therapeutic agents for hyperlipidemia, antihypertensive agents, antiobesity agents, diuretics, therapeutic agents for macular degeneration, antioxidants, nitric oxide inducing agents, matrix metalloproteinase (MMPs) inhibitors, anti-angiogenesis agents, chemotherapeutic agents, immunotherapeutic agents, antithrombotic agents, therapeutic agents for osteoporosis, antidementia agents, erectile dysfunction improving agents, therapeutic agents for incontinence, frequent urination, therapeutic agents for dysuria and the like (hereinafter to be abbreviated as combination drugs). These concomitant drugs may be low-molecular compounds, or high-molecular proteins, polypeptides, antibodies, vaccines or the like.

The time of administration of the compound of the present invention and that of the combination drug are not limited, and they may be administered simultaneously or in a staggered manner to the administration subject.

The administration form is not particularly limited, and the compound of the present invention and a concomitant drug only need to be combined. Examples of such administration mode include the following:

(1) administration of a single preparation obtained by simultaneously processing the compound of the present invention and the combination drug, (2) simultaneous administration of two kinds of preparations of the compound of the present invention and the combination drug, which have been separately produced, by the same administration route, (3) administration of two kinds of preparations of the compound of the present invention and the combination drug, which have been separately produced, by the same administration route in a staggered manner, (4) simultaneous administration of two kinds of preparations of the compound of the present invention and the combination drug, which have been separately produced, by different administration routes, (5) administration of two kinds of preparations of the compound of the present invention and the combination drug, which have been separately produced, by different administration routes in a staggered manner (e.g., administration in the order of the compound of the present invention and the combination drug, or in the reverse order).

The dose of the combination drug can be appropriately determined with the clinically-used dose as the standard. In addition, the mixing ratio of compound of the present invention and the combination drug can be appropriately determined according to the administration subject, administration route, target disease, symptom, combination and the like. For example, when the administration subject is human, 0.01 to 100 parts by weight of the combination drug can be used per 1 part by weight of the compound of the present invention.

The compound can be used in combination with a means for providing the patients with an additional or synergistic effect, for example, use of extracorporeal rheopheresis, use of a transplantable compact telescope, laser photocoagulation of drusen, a microstimulation therapy and the like.

Examples of the above-mentioned "therapeutic agent for diabetes" include insulin preparations (e.g., animal insulin preparations extracted from pancreas of bovine or swine; human insulin preparations genetically synthesized using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Netoglitazone (MCC-555), Rivoglitazone (CS-011), FK-614, compound described in WO 01/38325, Tesaglitazar (AZ-242), Ragaglitazar (NN-622), Muraglitazar (BMS-298585), Edaglitazone (BM-13-1258), Metaglidasen (MBX-102), Naveglitazar (LY-519818), MX-6054, LY-510929, AMG131 (T-131) or a salt thereof, THR-0921), α-glucosidase inhibitors (e.g., voglibose, acarbose, miglitol, emiglitate), biguanides (e.g., phenformin, metformin, buformin or a salt thereof (e.g., hydrochloride, fumarate, succinate)), insulin secretagogues [sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or calcium salt hydrate thereof], dipeptidyl peptidase IV inhibitors (e.g., Vildagliptin (LAF237), P32/98, Sitagliptin (MK-431), alogliptin, Trelagliptin, P93/01, PT-100, Saxagliptin (BMS-477118), BI1356, GRC8200, MP-513, PF-00734200, PHX1149, SK-0403, ALS2-0426, T-6666, TS-021, KRP-104), β3 agonists (e.g., AJ-9677), GPR40 agonist, GLP-1 receptor agonists [e.g., GLP-1, GLP-1MR agent, NN-2211, AC-2993 (exendin-4)), BIM-51077, Aib(8,35)hGLP-1(7,37)NH2, CJC-1131], amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists), SGLUT (sodium-glucose cotransporter) inhibitors (e.g., T-1095, dapagliflozin, remogliflozin), 11β-hydroxysteroid dehydrogenase inhibitors (e.g., BVT-3498), adiponectin or agonist thereof, IKK inhibitors (e.g., AS-2868), leptin resistance improving drugs, somatostatin receptor agonists (e.g., compounds described in WO 01/25228, WO 03/42204, WO 98/44921, WO 98/45285, WO 99/22735 etc.), glucokinase activators (e.g., Ro-28-1675), and ACC2 (acetyl-CoA carboxylase 2) inhibitor.

Examples of the "therapeutic agents for diabetic complications" include aldose reductase inhibitors (e.g., Tolrestat, Epalrestat, zenarestat, Zopolrestat, minalrestat, Fidarestat, CT-112, ranirestat (AS-3201)), neurotrophic factors and increasing drugs thereof (e.g., NGF, NT-3, BDNF, neurotrophin production-secretion promoters described in WO01/14372 (e.g., 4-(4-chlorophenyl)-2-(2-methyl-1-imidazolyl)-5-[3-(2-methylphenoxy)propyl]oxazole)), PKC inhibitors (e.g., ruboxistaurin mesylate), AGE inhibitors (e.g., ALT946, pimagedine, N-phenacylthiazolium bromide (ALT766), EXO-226, Pyridorin, Pyridoxamine), active oxygen scavengers (e.g., thioctic acid), cerebral vasodilators (e.g., tiapuride, mexiletine), somatostatin receptor agonists (BIM23190), and apoptosis signal regulating kinase-1 (ASK-1) inhibitors.

Examples of the "hyperlipidemia therapeutic agent" include statin compounds as cholesterol synthesis inhibitors (e.g., cerivastatin, pravastatin, simvastatin, lovastatin, rosuvastatin, atorvastatin, fluvastatin, pitavastatin or salts thereof (e.g., sodium salt, etc.) etc.), squalene synthetase inhibitors or fibrate compounds with hypotriglyceride action (e.g., bezafibrate, clofibrate, simfibrate, clinofibrate, etc.), cholesterol absorption inhibitors (e.g., zetia), anion-exchange resins (e.g., cholestyramine), probucol, nicotinic drugs (e.g., nicomol, niceritrol), phytosterols (e.g., soysterol, γ-oryzanol)), fish oil preparations (e.g., EPA, DHA, omacor), PPAR α-agonist, PPAR γ-agonist, PPAR δ-agonist, LXR agonist, FXR antagonist, FXR agonist, DGAT inhibitor, MGAT inhibitor, MTP inhibitor (e.g., lomitapide), and nucleic acid drugs containing ApoB antisense (e.g., mipomersen) or PCSK9 siRNA antisense oligonucleotide.

Examples of the antihypertensive agent include angiotensin converting enzyme inhibitors (e.g., captopril, enalapril, delapril and the like), angiotensin II antagonists (e.g., candesartan cilexetil, candesartan, azilsartan, azilsartan medoxomil, losartan, losartan potassium, eprosartan, valsartan, telmisartan, irbesartan, tasosartan, olmesartan, olmesartan medoxomil etc.), calcium antagonist (e.g., manidipine, nifedipine, amlodipine, efonidipine, nicardipine etc.), β-blocker (e.g., propranolol, nadolol, timolol, nipradilol, bunitrolol, indenolol, Penbutolol, carteolol, carvedilol, pindolol, acebutolol, atenolol, bisoprolol, metoprolol, labetalol, amosulalol, arotinolol etc.), and clonidine.

Examples of the "antiobesity agent" include monoamine uptake inhibitors (e.g., phentermine, sibutramine, mazindol, fluoxetine, tesofensine), serotonin 2C receptor agonists (e.g., lorcaserin), serotonin 6 receptor antagonists, histamine H3 receptor, GABA modulator (e.g., topiramate), neuropeptide Y antagonists (e.g., velneperit), cannabinoid receptor antagonists (e.g., rimonabant, taranabant), ghrelin antagonists, ghrelin receptor antagonists, ghrelin acylation enzyme inhibitors, opioid receptor antagonists (e.g., GSK-1521498), orexin receptor antagonists, melanocortin 4 receptor agonists, 11β-hydroxysteroid dehydrogenase inhibitors (e.g., AZD-4017), pancreatic lipase inhibitors (e.g., orlistat, cetilistat), β3 agonists (e.g., N-5984), diacylglycerol acyltransferase 1 (DGAT1) inhibitors, acetylCoA carboxylase (ACC) inhibitors, stearate CoA desaturase inhibitors, microsomal triglyceride transfer protein inhibitors (e.g., R-256918), Na-glucose cotransporter inhibitors (e.g., JNJ-28431754, remogliflozin), NFK inhibitors (e.g., HE-3286), PPAR agonists (e.g., GFT-505, DRF-11605), phosphotyrosine phosphatase inhibitors (e.g., sodium vanadate, Trodusquemin), GPR119 agonists (e.g., PSN-821), glucokinase activators (e.g., AZD-1656), leptin, leptin derivatives (e.g., metreleptin), CNTF (ciliary neurotrophic factor), BDNF (brain-derived neurotrophic factor), cholecystokinin agonists, glucagon-like peptide-1 (GLP-1) preparations (e.g., animal GLP-1 preparations extracted from the pancreas of bovine or swine; human preparations genetically synthesized using *Escherichia coli* or yeast; fragments or derivatives of GLP-1 (e.g., exenatide, liraglutide)), amylin preparations (e.g., pramlintide, AC-2307), neuropeptide Y agonists (e.g., PYY3-36, derivatives of PYY3-36, obineptide, TM-30339, TM-30335), oxyntomodulin preparations: FGF21 preparations (e.g., animal FGF21 preparations extracted from the pancreas of bovine or swine; human FGF21 preparations genetically synthesized using *Escherichia coli* or yeast; fragments or derivatives of FGF21), and anorexigenic agents (e.g., P-57).

Examples of the "diuretics" include xanthine derivatives (e.g., sodium salicylate and theobromine, calcium salicylate and theobromine), thiazide preparations (e.g., ethiazide, cyclopenthiazide, trichloromethiazide, hydrochlorothiazide, hydroflumethiazide, benzylhydrochlorothiazide, penflutizide, poly5thiazide, methyclothiazide), antialdosterone preparations (e.g., spironolactone, eplerenone, triamterene), carbonate dehydratase inhibitors (e.g., acetazolamide), chlorobenzenesulfonamide preparations (e.g., chlortalidone, mefruside, indapamide), azosemide, isosorbide, etacrynic acid, piretanide, bumetanide, and furosemide.

Examples of the therapeutic agent for macular degeneration include fenretinide (4-hydroxy(phenyl)retinamide), compound described in WO 2009/042444, negatively-charged phospholipid, particular mineral (e.g., copper-containing mineral such as copper oxide and the like, and zinc-containing mineral such as zinc oxide and the like, selenium-containing compound).

Examples of the antioxidant include vitamin C, vitamin E, β-carotene and other carotenoid, coenzyme Q, 4-hydroxy-2,2,6,6-tetramethylpiperidine-N-oxyl (also known as Tempol), lutein, butylated hydroxytoluene, resveratrol, trolox analogue (PNU-83836-E), and bilberry extract.

Examples of the nitric oxide inducing agent include L-arginine, L-homoarginine and N-hydroxy-L-arginine (e.g., nitrosated L-arginine, nitrosylated L-arginine, nitrosated N-hydroxy-L-arginine, nitrosylated N-hydroxy-L-arginine, nitrosated L-homoarginine, nitrosylated L-homoarginine), L-arginine precursor and/or physiologically acceptable salt thereof (e.g., citrulline, ornithine, glutamine, lysine), polypeptide containing at least one of the above-mentioned amino acids, enzyme arginase inhibitor (e.g., N-hydroxy-L-arginine and 2(S)-amino-6-boronohexanoic acid), and substrate for nitric oxide or closely-related derivative thereof.

Examples of the matrix metalloproteinase (MMPs) inhibitor include tissue inhibitors of metalloproteinase (TIMPs) (e.g., TIMP-1, TIMP-2, TIMP-3, TIMP-4), α2-macroglobulin, tetracycline (e.g., tetracycline, minocycline, doxycycline), hydroxamate (e.g., batimastat, MARIMISTAT, TROCADE), chelating agent (e.g., EDTA, cysteine, acetylcysteine, D-penicillamine, gold salt), synthetic MMP fragment, succinylmercaptopurine, phosphoramidate, and hydroxamic acid (hydroxaminic acid).

Examples of the anti-angiogenesis agent or anti-VEGF agent include Rhufab V2 (Lucentis), tryptophanyl-tRNA synthetase (TrpRS), Eye 001 (anti-VERG pegylated aptamer), squalamine, Retaane 15 mg (anecortave acetate for depot suspended product; Alcon, Inc.), Combretastain A4 prodrug (CA4P), Macugen, Mifeprex (mifepristone-ru486), sub-tenon triamcinolone acetonide, intravitreal crystalline triamcinolone acetonide, prinomastat (AG3340), fluocinolone acetonide (including fluocinolone intraocular implant), VEGFR inhibitor, and VEGF-trap.

Examples of the chemotherapeutic agents include alkylating agents (e.g., cyclophosphamide, ifosfamide), metabolic antagonists (e.g., methotrexate, 5-fluorouracil and derivative thereof), antitumor antibiotics (e.g., mitomycin, Adriamycin, etc.), plant-derived antitumor agents (e.g., vincristine, vindesine, Taxol), cisplatin, carboplatin, etoposide and the like. Of these, Furtulon or NeoFurtulon, which are 5-fluorouracil derivatives, and the like are preferable.

Examples of the above-mentioned "immunotherapeutic agents" include microorganism or bacterial components (e.g., muramyl dipeptide derivatives, Picibanil, etc.), polysaccharides having immunity potentiating activity (e.g., lentinan, schizophyllan, krestin, etc.), cytokines obtained by genetic engineering techniques (e.g., interferon, interleukin (IL), etc.), colony stimulating factors (e.g., granulocyte colony stimulating factor, erythropoietin, etc.) and the like, with preference given to interleukins such as IL-1, IL-2, IL-12 and the like.

Examples of the antithrombotic agent include heparin (e.g., heparin sodium, heparin calcium, dalteparin sodium), warfarin (e.g., warfarin potassium), anti-thrombin drug (e.g., aragatroban, dabigatran), thrombolytic agent (e.g., urokinase), tisokinase, alteplase, nateplase, monteplase, pamiteplase), platelet aggregation inhibitor (e.g., ticlopidine hydrochloride, cilostazol), ethyl icosapentate, beraprost sodium, sarpogrelate hydrochloride, prasugrel, E5555, SHC530348), FXa inhibitor (e.g., 1-(1-{(2S)-3-[(6-chloronaphthalen-2-yl)sulfonyl]-2-hydroxypropanoyl}piperidin-4-yl)tetrahydropyrimidin-2 (1H)-one, rivaroxaban, apixaban, DU-156, YM150).

Examples of the "therapeutic agents for osteoporosis" include alfacalcidol, calcitriol, elcaltonin, calcitonin salmon, estriol, ipriflavone, pamidronate disodium, alendronate sodium hydrate, and incadronate disodium.

Examples of the "antidementia agent" include tacrine, donepezil, rivastigmine, and galanthamine.

Examples of the erectile dysfunction improving drug include apomorphine, sildenafil citrate.

Examples of the therapeutic agents for urinary incontinence or pollakiuria include flavoxate hydrochloride, oxybutynin hydrochloride, propiverine hydrochloride.

Examples of the therapeutic agents for dysuria include acetylcholine esterase inhibitors (e.g., distigmine).

In addition, examples of the combination drug includes drugs having a cachexia-improving action established in animal models and clinical situations, such as cyclooxygenase inhibitors (e.g., indomethacin), progesterone derivatives (e.g., megestrol acetate), glucosteroids (e.g., dexamethasone), metoclopramide agents, tetrahydrocannabinol agents, fat metabolism improving agents (e.g., eicosapentanoic acid), growth hormones, IGF-1, or antibodies to a cachexia-inducing factor such as TNF-α, LIF, IL-6, oncostatin M.

Furthermore, examples of the combination drug includes nerve regeneration promoting drugs (e.g., Y-128, VX-853, prosaptide), antidepressant (e.g., desipramine, amitriptyline, imipramine), antiepileptic (e.g., lamotrigine), antiarrhythmic drugs (e.g., mexiletine), acetylcholine receptor ligand (e.g., ABT-594), endothelin receptor antagonist (e.g., ABT-627), monoamine uptake inhibitors (e.g., tramadol), narcotic analgesics (e.g., morphine), GABA receptor agonist (e.g., gabapentin), α2 receptor agonist (e.g., clonidine), topical analgesic (e.g., capsaicin), antianxiety drug (e.g., benzodiazepine), dopamine agonist (e.g., apomorphine), midazolam, ketoconazole and the like.

EXAMPLES

The present invention is explained in detail in the following by referring to Examples, Experimental Examples and Formulation Examples. However, the examples do not limit the present invention and the present invention can be modified within the scope of the present invention.

The "room temperature" in the following Examples is generally about 10° C. to about 35° C. The ratio for a mixed solvent is, unless otherwise specified, a volume mixing ratio and % means wt % unless otherwise specified.

In silica gel column chromatography, the indication of NH means use of aminopropylsilane-bonded silica gel and the indication of Diol means use of 3-(2,3-dihydroxypropoxy) propylsilane bond silica gel. In HPLC (high performance liquid chromatography), the indication of C18 means use of octadecyl-bonded silica gel. The ratio of elution solvents is, unless otherwise specified, a volume mixing ratio.

In the following Examples, the following abbreviations are used.

mp: melting point
MS: mass spectrum
M: molar concentration
$CDCl_3$: deuterated chloroform
DMSO: dimethyl sulfoxide
DMSO-$d_6$: deuterated dimethyl sulfoxide
$^1$H NMR: proton nuclear magnetic resonance
LC/MS: liquid chromatography mass spectrometer
ESI: electrospray ionization
APCI: atmospheric pressure chemical ionization
DME: 1,2-dimethoxyethane
DMA: N,N-dimethylacetamide
HATU: 2-(7-azabenzotriazol-1-yl)-1,1,3,3-tetramethyluronium hexafluorophosphate
HOBt: 1-hydroxybenzotriazole
THF: tetrahydrofuran
DMF: N,N-dimethylformamide
TFA: trifluoroacetic acid
LHMDS: hexamethyldisilazane lithium
n-: normal
s-: secondary
t-: tertiary $^1$H NMR was measured by Fourier-transform type NMR. For the analysis, ACD/SpecManager (trade name) and the like were used. Very mild peaks of protons of hydroxyl group, amino group and the like are not described.

MS was measured by LC/MS. As the ionization method, ESI method, or APCI method was used. The data indicates those found. Generally, molecular ion peak ([M+H]$^+$, [M–H]$^-$ and the like) is observed; however, when the compound has a tert-butoxycarbonyl group, a peak after elimination of a tert-butoxycarbonyl group or tert-butyl group may be observed as a fragment ion. When the compound has a hydroxyl group, a peak after elimination of $H_2O$ may be observed as a fragment ion. In the case of a salt, a molecular ion peak or fragment ion peak of free form is generally observed.

The unit of sample concentration (c) in optical rotation ($[\alpha]_D$) is g/100 mL.

Example 1

((2-(3,5-bis(trifluoromethyl)phenyl)pyrimidin-5-yl)oxy)acetic acid

A) tert-butyl 2-((2-chloropyrimidin-5-yl)oxy)acetate

To a mixture of 2-chloropyrimidin-5-ol (5.7 g), tert-butyl 2-bromoacetate (9.80 g) and DMF (75 mL) was added potassium phosphate (14.83 g) at room temperature, and the mixture was stirred at 50° C. for 2 hr. The reaction mixture was quenched with water at room temperature, and extracted with ethyl acetate. The extract was washed with water and saturated brine, dried over magnesium sulfate, and the solvent was evaporated under reduced pressure. The residue was purified by silica gel column chromatography (ethyl acetate/hexane) to give the title compound (10.57 g).

MS: [M+H]$^+$ 245.0.

B) tert-butyl 2-((2-(3,5-bis(trifluoromethyl)phenyl)pyrimidin-5-yl)oxy)acetate

To a mixture of tert-butyl 2-((2-chloropyrimidin-5-yl)oxy)acetate (10.5 g), (3,5-bis(trifluoromethyl)phenyl)boronic acid (16.60 g), potassium carbonate (11.86 g), water (30 mL) and DME (150 mL) was added tetrakis(triphenylphosphine)palladium (0) (2.479 g) at room temperature, and the mixture was stirred under a nitrogen atmosphere at 100° C. for 10 hr. The reaction mixture was diluted with water at room temperature, and extracted with ethyl acetate. The extract was washed with water and saturated brine, dried over magnesium sulfate, and the solvent was evaporated under reduced pressure. The residue was purified by silica gel column chromatography (NH, ethyl acetate/hexane) to give the title compound (7.35 g).

MS: [M+H]$^+$ 423.1.

C) ((2-(3,5-bis(trifluoromethyl)phenyl)pyrimidin-5-yl)oxy)acetic acid

To tert-butyl 2-((2-(3,5-bis(trifluoromethyl)phenyl)pyrimidin-5-yl)oxy)acetate (7.3 g) was added TFA (25 mL) at 0° C., and the mixture was stirred at room temperature for 3 hr. The solvent was evaporated from the reaction mixture under reduced pressure. The obtained solid was recrystallized from ethyl acetate/hexane to give the title compound (5.5 g).

$^1$H NMR (300 MHz, DMSO-d$_6$) δ 5.01 (2H, s), 8.26 (1H, s), 8.76 (2H, s), 8.82 (2H, s), 13.34 (1H, brs).

Example 2

((6-(3,5-bis(trifluoromethyl)phenyl)pyridin-3-yl)oxy)acetic acid A) 6-(3,5-bis(trifluoromethyl)phenyl)pyridin-3-ol To a mixture of 6-bromopyridin-3-ol (32 g), (3,5-bis(trifluoromethyl)phenyl)boronic acid (61.7 g), potassium carbonate (76 g), water (100 mL) and DME (500 mL) was added tetrakis(triphenylphosphine)palladium (0) (8.50 g) under a nitrogen atmosphere at room temperature, and the mixture was stirred under a nitrogen atmosphere at 100° C. for 10 hr. To the reaction mixture was added 2N hydrochloric acid (555 mL) at 0° C., and the mixture was extracted with ethyl acetate. The extract was washed with water and saturated brine, dried over magnesium sulfate, and the solvent was evaporated under reduced pressure. The residue was purified by silica gel column chromatography (ethyl acetate/hexane) to give the title compound (50 g).

MS: [M+H]$^+$ 308.0.

B) tert-butyl 2-((6-(3,5-bis(trifluoromethyl)phenyl)pyridin-3-yl)oxy)acetate

To a mixture of 6-(3,5-bis(trifluoromethyl)phenyl)pyridin-3-ol (40 g), tert-butyl 2-bromoacetate (30.5 g) and DMF (100 mL) was added potassium carbonate (36.0 g) at room temperature, and the mixture was stirred at room temperature overnight. The reaction mixture was quenched with water at room temperature, and extracted with ethyl acetate. The extract was washed with water and saturated brine, dried over magnesium sulfate, and the solvent was evaporated under reduced pressure. The residue was purified by silica gel column chromatography (NH, ethyl acetate/hexane) to give the title compound (47.8 g).

MS: [M+H]$^+$ 422.1.

C) ((6-(3,5-bis(trifluoromethyl)phenyl)pyridin-3-yl)oxy)acetic acid

To a mixture of tert-butyl 2-((6-(3,5-bis(trifluoromethyl)phenyl)pyridin-3-yl)oxy)acetate (0.999 g), THF (5 mL) and ethanol (10 mL) was added 1N aqueous sodium hydroxide solution (10 mL) at 0° C., and the mixture was stirred at room temperature for 1.5 hr. To the reaction mixture was added dropwise at 0° C. 1N hydrochloric acid (10 mL), and the mixture was stirred at room temperature for 1 hr. The resulting solid was collected by filtration, washed with water, and dried under reduced pressure. The obtained solid was dissolved in ethanol (8.0 mL)/water (0.9 mL) at 75° C., water (7.6 mL) was added dropwise at 75° C., and the mixture was stirred at 75° C. for 0.5 hr, and the mixture was stirred at room temperature overnight. The obtained solid was collected by filtration, washed with ethanol/water (=1/1) and water, and dried under reduced pressure to give the title compound (0.7758 g).

$^1$H NMR (300 MHz, DMSO-d$_6$) δ 4.88 (2H, s), 7.55 (1H, dd, J=9.1, 3.0 Hz), 8.11 (1H, s), 8.27 (1H, d, J=9.1 Hz), 8.46 (1H, d, J=2.6 Hz), 8.68 (2H, s), 13.20 (1H, brs).

Example 3

3-(3-(3,5-bis(trifluoromethyl)phenyl)-1H-pyrazol-1-yl)propanoic acid

A) (E)-1-(3,5-bis(trifluoromethyl)phenyl)-3-(dimethylamino)prop-2-en-1-one

A mixture of 1-(3,5-bis(trifluoromethyl)phenyl)ethanone (100 g) and N,N-dimethylformamide dimethyl acetal (259 mL) was stirred at 100° C. for 2 hr. After completion of the reaction, the reaction mixture was cooled to room temperature, and poured into ice water. The resulting solid was collected by filtration, washed with ice-cold water and petroleum ether, and dried under reduced pressure to give the title compound (200 g).

MS: [M+H]$^+$ 312.2.

B) 3-(3,5-bis(trifluoromethyl)phenyl)-1H-pyrazole

To a mixture of (E)-1-(3,5-bis(trifluoromethyl)phenyl)-3-(dimethylamino)prop-2-en-1-one (100 g) and acetic acid (1000 mL) was added hydrazine monohydrate (40.2 g) at room temperature, and the mixture was stirred at 100° C. for 2 hr. After completion of the reaction, the reaction mixture was cooled to room temperature, and poured into ice water. The resulting solid was collected by filtration, and washed with cold water. The obtained solid was dissolved in ethyl acetate, and washed with water and saturated brine, and dried over anhydrous sodium sulfate. The solvent was evaporated under reduced pressure to give the title compound (70 g).

MS: [M+H]$^+$ 281.1.

C) 3-(3-(3,5-bis(trifluoromethyl)phenyl)-1H-pyrazol-1-yl)propanenitrile

To a mixture of 3-(3,5-bis(trifluoromethyl)phenyl)-1H-pyrazole (140 g) and DMF (1680 mL) was added cesium carbonate (243.7 g) at 0° C., then 3-bromopropionitrile (83.73 g) was added 0° C., and the mixture was stirred at 70° C. for 2 hr. After completion of the reaction, the reaction mixture was cooled to room temperature, and poured into ice water. The resulting solid was collected by filtration, and washed with water. The obtained solid was dissolved in ethyl acetate, washed with saturated brine and water, dried over anhydrous sodium sulfate, and evaporated under reduced pressure. To the obtained solid was added diethyl ether, and the mixture was stirred for 20 min and filtered to give the title compound (113.2 g).

MS: [M+H]$^+$ 334.2.

D) 3-(3-(3,5-bis(trifluoromethyl)phenyl)-1H-pyrazol-1-yl)propanoic acid

To 6N hydrochloric acid (150 mL) was added 3-(3-(3,5-bis(trifluoromethyl)phenyl)-1H-pyrazol-1-yl)propanenitrile (2.8 g) at room temperature, and the mixture was stirred at 100° C. for hr. The reaction mixture was diluted with water at room temperature, and the mixture was extracted with ethyl acetate. The extract was washed with water and saturated brine, dried over magnesium sulfate, and the solvent was evaporated under reduced pressure. The obtained solid was recrystallized from ethyl acetate/hexane to give the title compound (2.60 g).

$^1$H NMR (300 MHz, DMSO-d$_6$) δ 2.87 (2H, t, J=6.8 Hz), 4.40 (2H, t, J=6.8 Hz), 7.07 (1H, d, J=2.3 Hz), 7.87 (1H, d, J=2.3 Hz), 8.00 (1H, s), 8.40 (2H, s), 12.43 (1H, s).

Example 4

((4-(3,5-bis(trifluoromethyl)phenyl)-1,3-oxazol-2-yl)oxy)acetic acid

A) 1-(3,5-bis(trifluoromethyl)phenyl)-2-bromoethanone

A mixture of 3',5'-bis(trifluoromethyl)acetophenone (100 g) and acetic acid (400 mL) was heated to 90° C., a catalytic amount of bromine was added, and the oil bath was removed. The remaining bromine (20 mL) was added, and the mixture was stirred at room temperature for 1 hr. After completion of the reaction, the reaction mixture was diluted with ice water. The resulting solid was collected by filtration, washed with ice-cold water, and dried under reduced pressure to give the title compound (110 g).

$^1$H NMR (300 MHz, CDCl$_3$) δ 4.46 (2H, d, J=1.4 Hz), 8.12 (1H, s), 8.43 (2H, s).

B) 1-(3,5-bis(trifluoromethyl)phenyl)-2-hydroxyethanone

To a mixture of 1-(3,5-bis(trifluoromethyl)phenyl)-2-bromoethanone (90 g) and methanol (450 mL) was added sodium formate (91.34 g) at 0° C., and the mixture was stirred at 50 to 55° C. for 6 hr. The reaction mixture was concentrated, diluted with ethyl acetate, filtered to remove the resulting solid, and the filtrate was concentrated under reduced pressure. The residue was purified by silica gel column chromatography (ethyl acetate/petroleum ether) to give the title compound (35 g).

MS: [M−H]$^+$ 271.2.

C) 2-(3,5-bis(trifluoromethyl)phenyl)-2-oxoethyl phenyl carbonate

To a mixture of 1-(3,5-bis(trifluoromethyl)phenyl)-2-hydroxyethanone (35 g) and THF (350 mL) was added pyridine (15.68 mL) at 0° C., phenyl chloroformate (30.4 g) was added at 0° C., and the mixture was stirred at room temperature until the reaction was completed. After completion of the reaction, the reaction mixture was diluted with ethyl acetate under a nitrogen atmosphere, and the solid was filtered and washed with ethyl acetate. The filtrate was concentrated under reduced pressure to give the title compound (45 g).

MS: [M+H]$^+$ 393.2.

D) 4-(3,5-bis(trifluoromethyl)phenyl)oxazol-2(3H)-one

To a mixture of 2-(3,5-bis(trifluoromethyl)phenyl)-2-oxoethyl phenyl carbonate (45 g) and acetic acid (450 mL) was added ammonium acetate (34.7 g) at room temperature, and the mixture was stirred at 140° C. for 1 hr. After completion of the reaction, the reaction mixture was diluted with ice water, and extracted with ethyl acetate. The extract was washed with saturated brine, and dried over anhydrous sodium sulfate. The solvent was evaporated under reduced pressure. The residue was purified by silica gel column chromatography (ethyl acetate/petroleum ether) to give the title compound (14 g).

MS: [M+H]$^+$ 298.2.

E) 4-(3,5-bis(trifluoromethyl)phenyl)-2-chlorooxazole

To a mixture of 4-(3,5-bis(trifluoromethyl)phenyl)oxazol-2(3H)-one (27 g) and phosphoryl chloride (37.48 mL) was added N,N-diethylaniline (13.56 g) at room temperature, and the mixture was stirred at 100° C. overnight. After completion of the reaction, the reaction mixture was diluted with ice water, and extracted with ethyl acetate. The extract was washed with saturated brine and water and the solvent was evaporated under reduced pressure. The residue was purified by silica gel column chromatography (ethyl acetate/petroleum ether) to give the title compound (20 g).

$^1$H NMR (400 MHz, CDCl$_3$) δ 7.85 (1H, s), 8.07 (1H, s), 8.14 (2H, s).

F) tert-butyl 2-((4-(3,5-bis(trifluoromethyl)phenyl)oxazol-2-yl)oxy)acetate

To a mixture of sodium hydride (5.07 g, 60% in oil) and THF (50 mL) was added a mixture of tert-butyl 2-hydroxyacetate (8.368 g) and THF (50 mL) at 0° C. Then, a mixture of 4-(3,5-bis(trifluoromethyl)phenyl)-2-chlorooxazole (20 g) and THF (100 mL) was added at 0° C., and the mixture was stirred at room temperature for 1 hr. After completion of the reaction, the reaction mixture was diluted with ice water, and extracted with ethyl acetate. The extract was washed with saturated brine, and dried over anhydrous sodium sulfate. The solvent was evaporated under reduced pressure. The residue was purified by silica gel column chromatography (ethyl acetate/petroleum ether) to give the title compound (18.2 g).
MS: $[M+H]^+$ 412.1.

G) ((4-(3,5-bis(trifluoromethyl)phenyl)-1,3-oxazol-2-yl)oxy)acetic acid

To a mixture of tert-butyl 2-((4-(3,5-bis(trifluoromethyl) phenyl)oxazol-2-yl)oxy)acetate (0.2 g), THF (1.0 mL) and methanol (1.0 mL) was added 2N aqueous sodium hydroxide solution (1.0 mL) at room temperature, and the mixture was stirred at room temperature for 1.5 hr. To the reaction mixture was added 1N hydrochloric acid (2.0 mL) at room temperature, and the mixture was poured into saturated brine, and extracted with ethyl acetate. The extract was dried over anhydrous sodium sulfate and the solvent was evaporated under reduced pressure. The obtained solid was diluted with ethyl acetate (0.2 mL) and heated to 50° C. Heptane (1.0 mL) was added dropwise at 50° C., and the mixture was stirred at 50° C. for 0.5 hr, and at room temperature overnight. The obtained solid was collected by filtration, washed with ethyl acetate/heptane (=1/10) and heptane, and dried under reduced pressure to give the title compound (0.12 g).
$^1$H NMR (300 MHz, DMSO-$d_6$) δ 5.04 (2H, s), 8.06 (1H, s), 8.32 (2H, s), 8.61 (1H, s), 13.42 (1H, brs).

Example 5

((1-(3,5-bis(trifluoromethyl)phenyl)-1H-pyrazol-3-yl)oxy)acetic acid

A) (3,5-bis(trifluoromethyl)phenyl)hydrazine

A mixture of (3,5-bis(trifluoromethyl)phenyl)hydrazine hydrochloride (300 g), water (1500 mL) and ethyl acetate (1500 mL) was cooled to 10 to 15° C., basified by adding sodium hydroxide (70 g), and the mixture was stirred at room temperature for 0.5 hr. After completion of the reaction, the reaction mixture was extracted with ethyl acetate. The extract was washed with saturated brine and water, dried over anhydrous sodium sulfate. The solvent was evaporated under reduced pressure to give the title compound (200.2 g).
MS: $[M+H]^+$ 245.0.

B) 1-(3,5-bis(trifluoromethyl)phenyl)-1H-pyrazol-3-ol

A mixture of (3,5-bis(trifluoromethyl)phenyl)hydrazine (100 g) and tert-butanol (1000 mL) was stirred at 30° C., and ethyl propiolate (46.25 g) was added. After cooling to 0° C., potassium tert-butoxide (92 g) was gradually added, and the mixture was stirred at room temperature for 48 hr. After completion of the reaction, the reaction mixture was quenched with ice water, ethyl acetate was added, and the mixture was stirred at room temperature for 20 min and extracted with ethyl acetate. The extract was washed with water and saturated brine, dried over anhydrous sodium sulfate and the solvent was evaporated under reduced pressure. The residue was purified by silica gel column chromatography (ethyl acetate/petroleum ether) to give the title compound (64.2 g).
MS: $[M+H]^+$ 297.1.

C) tert-butyl 2-((1-(3,5-bis(trifluoromethyl)phenyl)-1H-pyrazol-3-yl)oxy)acetate To a mixture of 1-(3,5-bis(trifluoromethyl)phenyl)-1H-pyrazol-3-ol (128 g) and DMF (2400 mL) was added potassium carbonate (119.35 g) at 0° C., and then tert-butyl 2-bromoacetate (92.78 g) was added, and the mixture was stirred at room temperature for 0.5 hr. After completion of the reaction, the reaction mixture was poured into ice water. The resulting solid was collected by filtration, washed with n-pentane, and a treatment with activated carbon and slurry wash with petroleum ether were performed to give the title compound (108.6 g).
MS: $[M+H]^+$ 411.1.

D) ((1-(3,5-bis(trifluoromethyl)phenyl)-1H-pyrazol-3-yl)oxy)acetic acid

To a mixture of tert-butyl 2-((1-(3,5-bis(trifluoromethyl) phenyl)-1H-pyrazol-3-yl)oxy)acetate (0.2 g), THF (2.0 mL) and methanol (1.0 mL) was added 2N aqueous sodium hydroxide solution (1.0 mL) at room temperature, and the mixture was stirred at room temperature for 1.5 hr. To the reaction mixture was added 1N hydrochloric acid (2.0 mL) at room temperature, and the mixture was poured into saturated brine, and extracted with ethyl acetate. The extract was dried over anhydrous sodium sulfate, and the solvent was evaporated under reduced pressure. The obtained solid was diluted with ethyl acetate (0.3 mL) and heated to 50° C. Heptane (1.5 mL) was added dropwise at 50° C., and the mixture was stirred at 50° C. for 0.5 hr and at room temperature overnight. The obtained solid was collected by filtration, washed with ethyl acetate/heptane (=1/10) and heptane, and dried under reduced pressure to give the title compound (0.137 g).
$^1$H NMR (300 MHz, DMSO-$d_6$) δ 4.78 (2H, s), 6.21 (1H, d, J=2.6 Hz), 7.92 (1H, s), 8.35 (2H, s), 8.71 (1H, d, J=2.6 Hz), 13.12 (1H, s).

Example 6 ethyl 2-((2-(3,5-bis(trifluoromethyl)phenyl)pyrimidin-5-yl)oxy)acetate

A) tert-butyl 2-((2-chloropyrimidin-5-yl)oxy)acetate

To a mixture of 2-chloropyrimidin-5-ol (5.7 g), tert-butyl 2-bromoacetate (9.80 g) and DMF (75 mL) was added potassium phosphate (14.83 g) at room temperature, and the mixture was stirred at 50° C. for 2 hr. The reaction mixture was quenched with water at room temperature, and extracted with ethyl acetate. The extract was washed with water and saturated brine, dried over magnesium sulfate, and the solvent was evaporated under reduced pressure. The residue was purified by silica gel column chromatography (ethyl acetate/hexane) to give the title compound (10.57 g).
MS: $[M+H]^+$ 245.0.

B) tert-butyl 2-((2-(3,5-bis(trifluoromethyl)phenyl) pyrimidin-5-yl)oxy)acetate

To a mixture of tert-butyl 2-((2-chloropyrimidin-5-yl) oxy)acetate (10.5 g), (3,5-bis(trifluoromethyl)phenyl)boronic acid (16.60 g), potassium carbonate (11.86 g), water (30 mL) and DME (150 mL) was added tetrakis(triphenylphosphine)palladium (0) (2.479 g) at room temperature, and the mixture was stirred under a nitrogen atmosphere at 100° C. for 10 hr. The reaction mixture was diluted with water at room temperature, and extracted with ethyl acetate. The extract was washed with water and saturated brine, dried over magnesium sulfate, and the solvent was evaporated under reduced pressure. The residue was purified by silica gel column chromatography (NH, ethyl acetate/hexane) to give the title compound (7.35 g).

MS: [M+H]$^+$ 423.1.

C) ((2-(3,5-bis(trifluoromethyl)phenyl)pyrimidin-5-yl)oxy)acetic acid

To tert-butyl 2-((2-(3,5-bis(trifluoromethyl)phenyl)pyrimidin-5-yl)oxy)acetate (7.3 g) was added TFA (25 mL) at 0° C., and the mixture was stirred at room temperature for 3 hr. Under reduced pressure, the solvent was evaporated from the reaction mixture. The obtained solid was recrystallized from ethyl acetate/hexane to give the title compound (5.5 g).

$^1$H NMR (300 MHz, DMSO-d$_6$) δ 5.01 (2H, s), 8.26 (1H, s), 8.76 (2H, s), 8.82 (2H, s), 13.34 (1H, brs).

D) ethyl 2-((2-(3,5-bis(trifluoromethyl)phenyl)pyrimidin-5-yl)oxy)acetate

To a mixture of ((2-(3,5-bis(trifluoromethyl)phenyl)pyrimidin-5-yl)oxy)acetic acid (100 mg) and ethanol (2.0 mL) was added concentrated sulfuric acid (2 μL) at room temperature, and the mixture was heated under reflux for 8 hr. The reaction mixture was diluted with ethyl acetate, added to saturated aqueous sodium hydrogen carbonate solution at room temperature, and the mixture was extracted with ethyl acetate. The extract was washed with water and saturated brine, dried over anhydrous sodium sulfate, and the solvent was evaporated under reduced pressure to give the title compound (104 mg).

$^1$H NMR (300 MHz, CDCl$_3$) δ 1.34 (3H, t, J=7.2 Hz), 4.32 (2H, q, J=7.2 Hz), 4.78 (2H, s), 7.94 (1H, s), 8.53 (2H, s), 8.87 (2H, s).

Example 7 methyl 2-((6-(3,5-bis(trifluoromethyl)phenyl)pyridin-3-yl)oxy)acetate

A) 6-(3,5-bis(trifluoromethyl)phenyl)pyridin-3-ol

To a mixture of 6-bromopyridin-3-ol (32 g), (3,5-bis(trifluoromethyl)phenyl)boronic acid (61.7 g), potassium carbonate (76 g), water (100 mL) and DME (500 mL) was added tetrakis(triphenylphosphine)palladium (0) (8.50 g) under a nitrogen atmosphere at room temperature, and the mixture was stirred under a nitrogen atmosphere at 100° C. for 10 hr. To the reaction mixture was added at 0° C. 2N hydrochloric acid (555 mL), and the mixture was extracted with ethyl acetate. The extract was washed with water and saturated brine, dried over magnesium sulfate, and the solvent was evaporated under reduced pressure.

The residue was purified by silica gel column chromatography (ethyl acetate/hexane) to give the title compound (50 g).

MS: [M+H]$^+$ 308.0.

B) methyl 2-((6-(3,5-bis(trifluoromethyl)phenyl)pyridin-3-yl)oxy)acetate

To a mixture of 6-(3,5-bis(trifluoromethyl)phenyl)pyridin-3-ol (7.31 g), methyl 2-bromoacetate (4.73 g) and DMF (75 mL) was added potassium carbonate (6.58 g) at room temperature, and the mixture was stirred at 50° C. for 2 hr. The reaction mixture was quenched with water at room temperature, and extracted with ethyl acetate. The extract was washed with water and saturated brine, dried over magnesium sulfate, and the solvent was evaporated under reduced pressure. The residue was purified by silica gel column chromatography (ethyl acetate/hexane) to give the title compound (6.46 g).

$^1$H NMR (300 MHz, CDCl$_3$) δ 3.85 (3H, s), 4.76 (2H, s), 7.33 (1H, dd, J=8.7, 3.0 Hz), 7.77 (1H, d, J=8.3 Hz), 7.87 (1H, s), 8.41 (2H, s), 8.43-8.49 (1H, m).

Example 8 ethyl 3-(3-(3,5-bis(trifluoromethyl)phenyl)-1H-pyrazol-1-yl)propanoate

A) (E)-1-(3,5-bis(trifluoromethyl)phenyl)-3-(dimethylamino)prop-2-en-1-one

A mixture of 1-(3,5-bis(trifluoromethyl)phenyl)ethanone (100 g) and N,N-dimethylformamide dimethyl acetal (259 mL) was stirred at 100° C. for 2 hr. After completion of the reaction, the reaction mixture was cooled to room temperature, and poured into ice water. The resulting solid was collected by filtration, washed with ice-cold water and petroleum ether, and dried under reduced pressure to give the title compound (200 g).

MS: [M+H]$^+$ 312.2.

B) 3-(3,5-bis(trifluoromethyl)phenyl)-1H-pyrazole

To a mixture of (E)-1-(3,5-bis(trifluoromethyl)phenyl)-3-(dimethylamino)prop-2-en-1-one (100 g) and acetic acid (1000 mL) was added hydrazine monohydrate (40.2 g) at room temperature, and the mixture was stirred at 100° C. for 2 hr. After completion of the reaction, the reaction mixture was cooled to room temperature, and poured into ice water. The resulting solid was collected by filtration, and washed with cold water. The obtained solid was dissolved in ethyl acetate, and washed with water and saturated brine, and dried over anhydrous sodium sulfate. The solvent was evaporated under reduced pressure to give the title compound (70 g).

MS: [M+H]$^+$ 281.1.

C) 3-(3-(3,5-bis(trifluoromethyl)phenyl)-1H-pyrazol-1-yl)propanenitrile

To a mixture of 3-(3,5-bis(trifluoromethyl)phenyl)-1H-pyrazole (140 g) and DMF (1680 mL) was added cesium carbonate (243.7 g) at 0° C., 3-bromopropionitrile (83.73 g) was added at 0° C., and the mixture was stirred at 70° C. for 2 hr. After completion of the reaction, the reaction mixture was cooled to room temperature, and poured into ice water. The resulting solid was collected by filtration, and washed with water. The obtained solid was dissolved in ethyl acetate, and washed with saturated brine and water, and dried over anhydrous sodium sulfate. The solvent was evaporated under reduced pressure. To the obtained solid was added diethyl ether, and the mixture was stirred for 20 min and filtered to give the title compound (113.2 g).
MS: [M+H]$^+$ 334.2.

D) 3-(3-(3,5-bis(trifluoromethyl)phenyl)-1H-pyrazol-1-yl)propanoic acid

To 6N hydrochloric acid (150 mL) was added 3-(3-(3,5-bis(trifluoromethyl)phenyl)-1H-pyrazol-1-yl)propanenitrile (2.8 g) at room temperature, and the mixture was stirred at 100° C. for hr. The reaction mixture was diluted with water at room temperature, and extracted with ethyl acetate. The extract was washed with water and saturated brine, dried over magnesium sulfate, and the solvent was evaporated under reduced pressure. The obtained solid was recrystallized from ethyl acetate/hexane to give the title compound (2.60 g).
$^1$H NMR (300 MHz, DMSO-d$_6$) δ 2.87 (2H, t, J=6.8 Hz), 4.40 (2H, t, J=6.8 Hz), 7.07 (1H, d, J=2.3 Hz), 7.87 (1H, d, J=2.3 Hz), 8.00 (1H, s), 8.40 (2H, s), 12.43 (1H, s).

E) ethyl 3-(3-(3,5-bis(trifluoromethyl)phenyl)-1H-pyrazol-1-yl)propanoate

To a mixture of 3-(3-(3,5-bis(trifluoromethyl)phenyl)-1H-pyrazol-1-yl)propanoic acid (301 mg) and ethanol (6.0 mL) was added concentrated sulfuric acid (3 μL) at room temperature, and the mixture was heated under reflux for 19 hr. The solvent was evaporated under reduced pressure, and the residue was diluted with ethyl acetate. Saturated aqueous sodium hydrogen carbonate solution was added at room temperature, and the mixture was extracted with ethyl acetate. The extract was washed with saturated brine, dried over anhydrous sodium sulfate and the solvent was evaporated under reduced pressure. The residue was purified by silica gel column chromatography (ethyl acetate/hexane) to give the title compound (319 mg).
$^1$H NMR (300 MHz, CDCl$_3$) δ 1.25 (3H, t, J=7.2 Hz), 2.96 (2H, t, J=6.4 Hz), 4.16 (2H, q, J=7.2 Hz), 4.48 (2H, t, J=6.6 Hz), 6.60 (1H, d, J=2.6 Hz), 7.53 (1H, d, J=2.3 Hz), 7.77 (1H, s), 8.21 (2H, s).

Example 9 methyl 2-((4-(3,5-bis(trifluoromethyl)phenyl)-1,3-oxazol-2-yl)oxy)acetate

A)
1-(3,5-bis(trifluoromethyl)phenyl)-2-bromoethanone

A mixture of 3',5'-bis(trifluoromethyl)acetophenone (100 g) and acetic acid (400 mL) was heated in an oil bath to 90° C. A catalytic amount of bromine was added and the oil bath was removed. The remaining bromine (20 mL) was added, and the mixture was stirred at room temperature for 1 hr. After completion of the reaction, the reaction mixture was diluted with ice water. The resulting solid was collected by filtration, washed with ice-cold water, and dried under reduced pressure to give the title compound (110 g).
$^1$H NMR (300 MHz, CDCl$_3$) δ 4.46 (2H, d, J=1.4 Hz), 8.12 (1H, s), 8.43 (2H, s).

B) 1-(3,5-bis(trifluoromethyl)phenyl)-2-hydroxyethanone

To a mixture of 1-(3,5-bis(trifluoromethyl)phenyl)-2-bromoethanone (90 g) and methanol (450 mL) was added sodium formate (91.34 g) at 0° C., and the mixture was stirred at 50 to 55° C. for 6 hr. The reaction mixture was concentrated, diluted with ethyl acetate, and filtered to remove the resulting solid. The filtrate was concentrated under reduced pressure. The residue was purified by silica gel column chromatography (ethyl acetate/petroleum ether) to give the title compound (35 g).
MS: [M–H]$^+$ 271.2.

C) 2-(3,5-bis(trifluoromethyl)phenyl)-2-oxoethyl phenyl carbonate

To a mixture of 1-(3,5-bis(trifluoromethyl)phenyl)-2-hydroxyethanone (35 g) and THF (350 mL) was added pyridine (15.68 mL) at 0° C., phenyl chloroformate (30.4 g) was added at 0° C., and the mixture was stirred at room temperature until the reaction was completed. After completion of the reaction, under a nitrogen atmosphere, the reaction mixture was diluted with ethyl acetate, and the solid was filtrated, washed with ethyl acetate, and the filtrate was concentrated under reduced pressure to give the title compound (45 g).
MS: [M+H]$^+$ 393.2.

D) 4-(3,5-bis(trifluoromethyl)phenyl)-1,3-oxazol-2(3H)-one

To a mixture of 2-(3,5-bis(trifluoromethyl)phenyl)-2-oxoethyl phenyl carbonate (45 g) and acetic acid (450 mL) was added ammonium acetate (34.7 g) at room temperature, and the mixture was stirred at 140° C. for 1 hr. After completion of the reaction, the reaction mixture was diluted with ice water, and extracted with ethyl acetate. The extract was washed with saturated brine, and dried over anhydrous sodium sulfate. The solvent was evaporated under reduced pressure. The residue was purified by silica gel column chromatography (ethyl acetate/petroleum ether) to give the title compound (14 g).
MS: [M+H]$^+$ 298.2.

E) 4-(3,5-bis(trifluoromethyl)phenyl)-2-chloro-1,3-oxazole

To a mixture of 4-(3,5-bis(trifluoromethyl)phenyl)-1,3-oxazol-2(3H)-one (27 g) and phosphoryl chloride (37.48 mL) was added N,N-diethylaniline (13.56 g) at room temperature, and the mixture was stirred at 100° C. overnight. After completion of the reaction, the reaction mixture was diluted with ice water, and extracted with ethyl acetate. The extract was washed with saturated brine and water, and the solvent was evaporated under reduced pressure. The residue was purified by silica gel column chromatography (ethyl acetate/petroleum ether) to give the title compound (20 g).
$^1$H NMR (400 MHz, CDCl$_3$) δ 7.85 (1H, s), 8.07 (1H, s), 8.14 (2H, s).

F) methyl 2-((4-(3,5-bis(trifluoromethyl)phenyl)-1,3-oxazol-2-yl)oxy)acetate

To a mixture of sodium hydride (124 mg, 60% in oil) and THF (10 mL) was added a mixture of methyl 2-hydroxyacetate (186 mg) and THF (3 mL) at 0° C., then a mixture of 4-(3,5-bis(trifluoromethyl)phenyl)-2-chloro-1,3-oxazole (650 mg) and THF (3 mL) was added at 0° C., and the mixture was stirred at room temperature for 1 hr. After completion of the reaction, the reaction mixture was poured into ice-cold water, and the mixture was extracted with ethyl acetate. The extract was washed with saturated brine, dried over anhydrous sodium sulfate, and the solvent was evaporated under reduced pressure. The residue was purified by silica gel column chromatography (ethyl acetate/petroleum ether) to give the title compound (200 mg).

$^1$H NMR (400 MHz, CDCl$_3$) δ 3.85 (3H, s), 5.04 (2H, s), 7.69 (1H, s), 7.78 (1H, s), 8.06 (2H, d, J=1.7 Hz).

Example 10 methyl 2-((1-(3,5-bis(trifluoromethyl)phenyl)-1H-pyrazol-3-yl)oxy)acetate

A) (3,5-bis(trifluoromethyl)phenyl)hydrazine

A mixture of (3,5-bis(trifluoromethyl)phenyl)hydrazine hydrochloride (300 g), water (1500 mL) and ethyl acetate (1500 mL) was cooled to 10 to 15° C., basified by adding sodium hydroxide (70 g), and the mixture was stirred at room temperature for 0.5 hr. After completion of the reaction, the reaction mixture was extracted with ethyl acetate. The extract was washed with saturated brine and water, dried over anhydrous sodium sulfate and the solvent was evaporated under reduced pressure to give the title compound (200.2 g).

MS: [M+H]$^+$ 245.0.

B) 1-(3,5-bis(trifluoromethyl)phenyl)-1H-pyrazol-3-ol

A mixture of (3,5-bis(trifluoromethyl)phenyl)hydrazine (100 g) and tert-butanol (1000 mL) was stirred at 30° C., and ethyl propiolate (46.25 g) was added. After cooling to 0° C., potassium tert-butoxide (92 g) was gradually added, and the mixture was stirred at room temperature for 48 hr. After completion of the reaction, the reaction mixture was quenched with ice water, ethyl acetate was added, and the mixture was stirred at room temperature for 20 min and extracted with ethyl acetate. The extract was washed with water and saturated brine, dried over anhydrous sodium sulfate and the solvent was evaporated under reduced pressure. The residue was purified by silica gel column chromatography (ethyl acetate/petroleum ether) to give the title compound (64.2 g).

MS: [M+H]$^+$ 297.1.

C) methyl 2-((1-(3,5-bis(trifluoromethyl)phenyl)-1H-pyrazol-3-yl)oxy)acetate

To a mixture of 1-(3,5-bis(trifluoromethyl)phenyl)-1H-pyrazol-3-ol (800 mg) and DMF (10 mL) was added potassium carbonate (745 mg) at 0° C., then methyl 2-bromoacetate (454 mg) was added, and the mixture was stirred at room temperature for 0.5 hr. After completion of the reaction, the reaction mixture was poured into ice-cold water. The resulting solid was collected by filtration, and washed with n-pentane to give the title compound (730 mg).

$^1$H NMR (300 MHz, DMSO-d$_6$) δ 3.71 (3H, s), 4.95 (2H, s), 6.26 (1H, d, J=2.7 Hz), 7.93 (1H, s), 8.35 (1H, d, J=1.5 Hz), 8.72 (2H, d, J=2.8 Hz).

According to the methods shown in the above-mentioned Examples or a method analogous thereto, the Example compounds in the following Tables were produced. The Example compounds are shown in the following Tables. In the Tables, MS shows measured values.

TABLE 1

| Ex. No. | IUPAC name | structural formula | MS |
|---|---|---|---|
| 1 | ((2-(3,5-bis(trifluoromethyl)phenyl)pyrimidin-5-yl)oxy)acetic acid | | 364.9 |
| 2 | ((6-(3,5-bis(trifluoromethyl)phenyl)pyridin-3-yl)oxy)acetic acid | | 366.0 |

TABLE 1-continued

| Ex. No. | IUPAC name | structural formula | MS |
|---|---|---|---|
| 3 | 3-(3-(3,5-bis(trifluoromethyl)phenyl)-1H-pyrazol-1-yl)propanoic acid | | 350.9 |
| 4 | ((4-(3,5-bis(trifluoromethyl)phenyl)-1,3-oxazol-2-yl)oxy)acetic acid | | 353.8 |
| 5 | ((1-(3,5-bis(trifluoromethyl)phenyl)-1H-pyrazol-3-yl)oxy)acetic acid | | 352.9 |
| 6 | ethyl 2-((2-(3,5-bis(trifluoromethyl)phenyl)pyrimidin-5-yl)oxy)acetate | | 395.1 |
| 7 | methyl 2-((6-(3,5-bis(trifluoromethyl)phenyl)pyridin-3-yl)oxy)acetate | | 380.2 |

TABLE 1-continued

| Ex. No. | IUPAC name | structural formula | MS |
|---|---|---|---|
| 8 | ethyl (3-(3,5-bis(trifluoromethyl)phenyl)-1H-pyrazol-1-yl)propanoate | | 381.1 |
| 9 | methyl 2-((4-(3,5-bis(trifluoromethyl)phenyl)-1,3-oxazol-2-yl)oxy)acetate | | 370.2 |
| 10 | methyl 2-((1-(3,5-bis(trifluoromethyl)phenyl)-1H-pyrazol-3-yl)oxy)acetate | | 369.0 |

Reference Example 1 ethyl ((4-(3,5-bis(trifluoromethyl)phenyl)-1,3-oxazol-2-yl)sulfanyl)acetate

To a mixture of THF (6 mL) and sodium hydride (114 mg, 60% in oil) was added a mixture of ethyl thioglycolate (571 mg) and THF (2 mL) at 0° C., and the mixture was stirred for 15 min. Then, a mixture of 4-(3,5-bis(trifluoromethyl) phenyl)-2-chloro-1,3-oxazole (1 g) and THF (2 mL) was added at 0° C., and the mixture was stirred at room temperature for 1 hr. The reaction mixture was poured into ice-cooled water, and the mixture was extracted with ethyl acetate. The extract was washed with saturated brine, dried over sodium sulfate and the solvent was evaporated under reduced pressure. The residue was purified by silica gel column chromatography (ethyl acetate/petroleum ether) to give the title compound (1 g).
MS: [M+H]$^+$ 400.1.

Reference Example 2

((4-(3,5-bis(trifluoromethyl)phenyl)-1,3-oxazol-2-yl) sulfanyl)acetic acid

To a mixture of ethyl ((4-(3,5-bis(trifluoromethyl)phenyl)-1,3-oxazol-2-yl)sulfanyl)acetate (100 mg) and THF (2 mL) was added a mixture of lithium hydroxide (31.5 mg) and water (0.5 mL) at room temperature, and the mixture was stirred at room temperature for 1 hr. The reaction mixture was concentrated under reduced pressure, and the residue was diluted with water, acidified with concentrated hydrochloric acid at 0° C. and the mixture was stirred for 15 min. The precipitate was collected by filtration, dried under reduced pressure, and washed with petroleum ether to give the title compound (66 mg).
$^1$H NMR (300 MHz, DMSO-$d_6$) δ 4.10 (2H, s), 8.07 (1H, s), 8.39 (2H, s), 9.01 (1H, s).

Reference Example 3 ethyl ((6-(3,5-bis(trifluoromethyl)phenyl)pyridin-3-yl)sulfanyl)acetate

A) 2-(3,5-bis(trifluoromethyl)phenyl)-5-fluoropyridine

To a mixture of 2-bromo-5-fluoropyridine (1 g), toluene (10 mL) and ethanol (2 mL) were added (3,5-bis(trifluoromethyl)phenyl)boronic acid (1.759 g) and potassium phosphate (1.8 g) at room temperature, and the mixture was deaerated with argon for 20 min.
Tetrakis(triphenylphosphine)palladium (0) (33 mg) was added at room temperature, and the mixture was stirred at 80° C. overnight. The reaction mixture was filtered through celite, and the filtrate was diluted with water, and extracted with ethyl acetate. The extract was washed with water and saturated brine, dried over sodium sulfate, and the solvent was evaporated under reduced pressure. The residue was purified by silica gel column chromatography (ethyl acetate/ hexane) to give the title compound (1.6 g).
MS: [M+H]$^+$ 310.1.

B) ethyl ((6-(3,5-bis(trifluoromethyl)phenyl)pyridin-3-yl)sulfanyl)acetate

To a mixture of 2-(3,5-bis(trifluoromethyl)phenyl)-5-fluoropyridine (1 g), DMF (5 mL) and DMSO (5 mL) were added sodium hydrogen sulfide monohydrate (900 mg), sodium sulfide 9 hydrate (3.88 g) and diazabicycloundecene (1 g) at room temperature, and the mixture was stirred at 100° C. for 12 hr. The reaction mixture was cooled to room temperature, tributylphosphine (50% ethyl acetate solution, 10 mL) was added, and the mixture was stirred at room temperature for 18 hr. The reaction mixture was quenched with water, and extracted with ethyl acetate. The extract was washed with water and saturated brine, dried over sodium sulfate and the solvent was evaporated under reduced pressure. The residue was dissolved in DMF (5 mL), potassium carbonate (535 mg) was added at room temperature, and the mixture was stirred for 10 min. Ethyl 2-bromoacetate (309 mg) was added at room temperature, and the mixture was stirred for 12 hr. The reaction mixture was quenched with ice water, and extracted with ethyl acetate. The extract was washed with water and saturated brine, dried over sodium sulfate and the solvent was evaporated under reduced pressure. The residue was purified by silica gel column chromatography (ethyl acetate/petroleum ether) to give the title compound (152 mg).
MS: [M+H]$^+$ 410.1.

Reference Example 4

((6-(3,5-bis(trifluoromethyl)phenyl)pyridin-3-yl)sulfanyl)acetic acid

To a mixture of ethyl ((6-(3,5-bis(trifluoromethyl)phenyl)pyridin-3-yl)sulfanyl)acetate (100 mg), THF (2 mL) and water (0.5 mL) was added lithium hydroxide monohydrate (30 mg) at room temperature, and the mixture was stirred at room temperature for 2 hr. The reaction mixture was quenched with water, and concentrated under reduced pressure. The residue was diluted with water, and washed with ethyl acetate. The aqueous layer was acidified with 3 M hydrochloric acid at 0° C. The precipitate was collected by filtration, dried under reduced pressure, and washed with pentane to give the title compound (50 mg).
$^1$H NMR (400 MHz, DMSO-d$_6$) δ 3.97 (2H, s), 7.95 (1H, dd, J=8.3, 2.5 Hz), 8.16 (1H, s), 8.28 (1H, d, J=8.8 Hz), 8.68 (1H, d, J=2.4 Hz), 8.73 (2H, s), 12.99 (1H, brs).

Reference Example 5

3-(3-(3,5-bis(trifluoromethyl)phenyl)-1H-pyrazol-1-yl)butanoic acid

A) 3-(3-(3,5-bis(trifluoromethyl)phenyl)-1H-pyrazol-1-yl)butanenitrile

To a mixture of 3-(3-(3,5-bis(trifluoromethyl)phenyl)-1H-pyrazole (300 mg) and DMF (5 mL) was added cesium carbonate (872 mg), and the mixture was cooled to 0° C. 3-Bromobutanenitrile (0.129 mL) was added at 0° C., and the mixture was stirred at 70° C. for 2 hr. The reaction mixture was poured into ice water at room temperature. The resulting solid was collected by filtration, washed with water, and dried under reduced pressure to give the title compound (300 mg).
MS: [M+H]$^+$ 348.2.

B) 3-(3-(3,5-bis(trifluoromethyl)phenyl)-1H-pyrazol-1-yl)butanoic acid

To a mixture of 3-(3-(3,5-bis(trifluoromethyl)phenyl)-1H-pyrazol-1-yl)butanenitrile (300 mg) and acetic acid (5 mL) was added 6N hydrochloric acid (5 mL), and the mixture was heated under reflux for 24 hr. The reaction mixture was concentrated under reduced pressure, water was added to the obtained residue, and the mixture was extracted with ethyl acetate. The extract was washed with water and saturated brine, dried over anhydrous sodium sulfate, and concentrated under reduced pressure. The residue was purified by HPLC (C18, mobile phase: water/acetonitrile (0.1% HCO$_2$H containing system)) to give the title compound (110 mg).
MS: [M+H]$^+$ 367.0.
$^1$H NMR (400 MHz, DMSO-d$_6$) δ 1.49 (3H, d, J=6.8 Hz), 2.75-2.87 (1H, m), 2.89-3.00 (1H, m), 4.74-4.88 (1H, m), 7.06 (1H, d, J=2.4 Hz), 7.93 (1H, d, J=2.0 Hz), 8.00 (1H, s), 8.40 (2H, s), 12.35 (1H, brs).

Reference Example 6

1-((3-(3,5-bis(trifluoromethyl)phenyl-1H-pyrazol-1-yl)methyl)cyclopropanecarboxylic acid A) 1-((3-(3,5-bis(trifluoromethyl)phenyl-1H-pyrazol-1-yl)methyl)cyclopropanecarbonitrile To a mixture of 3-(3,5-bis(trifluoromethyl)phenyl)-1H-pyrazole (300 mg), cesium carbonate (872 mg) and DMF (5 mL) was added dropwise 1-(bromomethyl)cyclopropanecarbonitrile (205 mg) at 0° C., and the mixture was stirred at 70° C. for 2 hr. The reaction mixture was poured into ice water at room temperature. The resulting solid was collected by filtration, washed with water and dried under reduced pressure to give the title compound (310 mg).
MS: [M+H]$^+$ 360.1.

B) 1-((3-(3,5-bis(trifluoromethyl)phenyl-1H-pyrazol-1-yl)methyl)cyclopropanecarboxylic acid To a mixture of 1-((3-(3,5-bis(trifluoromethyl)phenyl-1H-pyrazol-1-yl)methyl)cyclopropanecarbonitrile (310 mg) and acetic acid (5 mL) was added 6N hydrochloric acid (5 mL), and the mixture was heated under reflux for 24 hr. The reaction mixture was concentrated under reduced pressure, water was added to the obtained residue, and the mixture was extracted with ethyl acetate. The extract was washed with water and saturated brine, dried over anhydrous sodium sulfate, and concentrated under reduced pressure. The residue was purified by HPLC (C18, mobile phase: water/acetonitrile (0.1% HCO$_2$H containing system)) to give the title compound (180 mg).
$^1$H NMR (400 MHz, DMSO-d$_6$) δ 1.07-1.16 (2H, m), 1.16-1.26 (2H, m), 4.41 (2H, s), 7.07 (1H, d, J=2.4 Hz), 7.87 (1H, d, J=2.4 Hz), 8.00 (1H, s), 8.40 (2H, s), 12.56 (1H, brs).

Reference Example 7

3-(3-(3,5-bis(trifluoromethyl)phenyl)-1H-pyrazol-1-yl)-2-methylpropanoic acid

To a mixture of 3-(3,5-bis(trifluoromethyl)phenyl)-1H-pyrazole (500 mg), cesium carbonate (1.45 g) and DMF (10 mL) was added dropwise 3-bromo-2-methylpropanoic acid (357 mg) at 0° C., and the mixture was stirred at 70° C. for 2 hr. To the reaction mixture was added water, and the mixture was extracted with ethyl acetate. The extract was washed with water and saturated brine, dried over anhydrous sodium sulfate, and concentrated under reduced pressure.

The residue was purified by HPLC (C18, mobile phase: water/acetonitrile (0.1% containing system)) to give the title compound (45 mg).

$^1$H NMR (400 MHz, DMSO-$d_6$) δ 1.06 (3H, d, J=6.8 Hz), 2.94-3.08 (1H, m), 4.23 (1H, dd, J=13.6, 6.8 Hz), 4.43 (1H, dd, J=13.6, 6.8 Hz), 7.07 (1H, d, J=2.0 Hz), 7.86 (1H, d, J=2.0 Hz), 8.01 (1H, s), 8.40 (2H, s), 12.53 (1H, brs).

According to the methods shown in the above-mentioned Reference Examples or a method analogous thereto, the Reference Example compounds in the following Tables were produced. The Reference Example compounds are shown in the following Tables. In the Tables, MS shows measured values.

TABLE 2

| Ref. Ex. No. | IUPAC name | structural formula | MS |
|---|---|---|---|
| 1 | ethyl ((4-(3,5-bis(trifluoromethyl)phenyl)-1,3-oxazol-2-yl)sulfanyl)acetate | | 400.1 |
| 2 | ((4-(3,5-bis(trifluoromethyl)phenyl)-1,3-oxazol-2-yl)sulfanyl)acetic acid | | 369.9 |
| 3 | ethyl ((6-(3,5-bis(trifluoromethyl)phenyl)pyridin-3-yl)sulfanyl)acetate | | 410.1 |
| 4 | ((6-(3,5-bis(trifluoromethyl)phenyl)pyridin-3-yl)sulfanyl)acetic acid | | 382.0 |
| 5 | 3-(3-(3,5-bis(trifluoromethyl)phenyl)-1H-pyrazol-1-yl)butanoic acid | | 364.9 |

TABLE 2-continued

| Ref. Ex. No. | IUPAC name | structural formula | MS |
|---|---|---|---|
| 6 | 1-((3-(3,5-bis(trifluoromethyl)phenyl)-1H-pyrazol-1-yl)methyl)cyclopropane-carboxylic acid | | 376.9 |
| 7 | 3-(3-(3,5-bis(trifluoromethyl)phenyl)-1H-pyrazol-1-yl)-2-methyl propanoic acid | | 364.9 |

Experimental Example 1

Using the Retinol-RBP4-TTR ELISA system shown below, the action of the compound of the present invention to inhibit the binding of RBP4 and retinol and TTR was evaluated.

1A: Cloning of Human RBP4 Gene and Human TTR Gene

Human RBP4 gene was cloned by PCR using human Universal cDNA (Clontech, QUICK-Clone cDNA) as a template, and the following primer sets.

```
RBPU:
                                     (SEQ ID NO: 1)
5'-ATATGGATCCACCATGAAGTGGGTGTGGGCGCTC-3'

RBPL:
                                     (SEQ ID NO: 2)
5'-ATATGCGGCCGCCTACAAAAGGTTTCTTTCTGATCTGC-3'
```

PCR reaction was performed according to the protocol attached to Pyrobest polymerase (TAKARA BIO INC., LTD.). The obtained PCR product was subjected to agarose gel (1%) electrophoresis, an about 0.6 kb DNA fragment containing RBP4 gene was recovered from the gel, digested with restriction enzymes BamHI and NotI. DNA fragment after the restriction enzyme treatment was subjected to agarose gel (1%) electrophoresis, an about 0.6 kb DNA fragment was recovered, and ligated to plasmid pcDNA3.1 (+) (Invitrogen) digested with restriction enzymes BamHI and NotI to give an expression plasmid pcDNA3.1(+)/hRBP4. The DNA sequence of the inserted fragment was confirmed to have matched with the object sequence.

Human TTR gene was cloned by PCR reaction using human small intestine cDNA (Clontech, QUICK-Clone cDNA) as a template, and the following primer sets.

```
TTRU:
                                     (SEQ ID NO: 3)
5'-ATATGGATCCACCATGGCTTCTCATCGTCTGCTCC-3'

TTRL:
                                     (SEQ ID NO: 4)
5'-ATATGCGGCCGCTCATTCCTTGGGATTGGTGACGA-3'
```

PCR reaction was performed according to the protocol attached to Pyrobest polymerase (TAKARA BIO INC., LTD.). The obtained PCR product was subjected to agarose gel (1%) electrophoresis, a 0.5 kb DNA fragment containing TTR gene was recovered from the gel, digested with restriction enzymes BamHI and NotI. DNA fragment after the restriction enzyme treatment was subjected to agarose gel (1%) electrophoresis, an about 0.5 kb DNA fragment was recovered, and ligated to plasmid pcDNA3.1(+) (Invitrogen) digested with restriction enzymes BamHI and NotI to give an expression plasmid pcDNA3.1(+)/hTTR. The DNA sequence of the inserted fragment was confirmed to have matched with the object sequence.

1B: Construction of Human RBP4-his Expression Plasmid

EcoRI site was introduced into the 3'-end of hRBP4 gene by PCR using the expression plasmid pcDNA3.1(+)/hRBP4 prepared in the above-mentioned 1A as a template and the following primer sets.

```
CMVP:
                                     (SEQ ID NO: 5)
5'-TGGGAGGTCTATATAAGCAGAGCTCG-3'

RBPECO:
                                     (SEQ ID NO: 6)
5'-ATATGAATTCTTCCTTGGGATTGGTGAC-3'
```

PCR was performed according to the protocol attached to Z-Taq polymerase (TAKARA BIO INC., LTD.). The obtained PCR product was purified by QIAquick PCR purification Kit (QIAGEN), and digested with restriction enzymes BamHI and EcoRI. DNA fragment after the restriction enzyme treatment was subjected to agarose gel (1%) electrophoresis, the obtained about 0.6 kb DNA fragment was recovered, and ligated to plasmid pcDNA3.1(+) (Invitrogen) digested with restriction enzymes BamHI and EcoRI to give pcDNA3.1(+)/hRBP4-Eco having EcoRI site at the 3'-end of hRBP4 gene.

EcoRI site was introduced into the 3'-end of hTTR gene by PCR using the expression plasmid pcDNA3.1(+)/hTTR prepared in the above-mentioned 1A as a template and CMVP and TTRECO primer sets.

```
TTRECO:
                              (SEQ ID NO: 7)
5'-ATATGAATTCCAAAAGGTTTCTTTCTGATC-3'
```

PCR reaction was performed according to the protocol attached to Z-Taq polymerase (TAKARA BIO INC., LTD.). The obtained PCR product was purified by QIAquick PCR purification Kit (QIAGEN), and digested with restriction enzymes BamHI and EcoRI. DNA fragment after the restriction enzyme treatment was subjected to agarose gel (1%) electrophoresis, the obtained about 0.6 kb DNA fragment was recovered, and ligated to plasmid pcDNA3.1(+) (Invitrogen) digested with restriction enzymes BamHI and EcoRI to give pcDNA3.1(+)/hTTR-Eco having EcoRI site at the 3'-end of hTTR gene.

TTR-His expression plasmid pcDNA3.1(+)/hTTR-His wherein His tag is added to the C-terminal of human TTR was prepared by inserting a synthetic DNA fragment containing His tag sequence prepared by annealing the following oligoDNA into the EcoRI site and NotI site of pcDNA3.1(+)/hTTR-Eco prepared as mentioned above.

```
HISENU:
                              (SEQ ID NO: 8)
5'-AATTCCATCATCATCATCATCACTAGGC-3'

HISENL:
                              (SEQ ID NO: 9)
5'-GGCCGCCTAGTGATGATGATGATGATGG-3'
```

HISENU and HISENL were each dissolved at a concentration of 25 pmole/uL, heated at 94° C. for 5 min, cooled to room temperature to allow for annealing, whereby synthetic DNA fragment containing His tag sequence was obtained. pcDNA3.1(+)/hTTR-Eco was digested with EcoRI and NotI, the DNA fragment after the restriction enzyme treatment was subjected to agarose gel (1%) electrophoresis, the obtained about 5.9 kb DNA fragment was recovered, and a synthetic DNA fragment containing His tag sequence was ligated thereto to give TTR-His expression plasmid pcDNA3.1(+)/hTTR-His wherein His tag is added to the C-terminal of human TTR.

RBP4-His expression plasmid pcDNA3.1(+)/hRBP4-His wherein His tag is added to the C-terminal of human RBP4 was prepared as follows. pcDNA3.1(+)/hRBP4-Eco was digested with restriction enzymes EcoRI and DraIII, subjected to agarose gel (1%) electrophoresis, and the obtained about 6.0 kb DNA fragment was recovered. pcDNA3.1(+)/hTTR-His was digested with restriction enzymes EcoRI and DraIII, subjected to agarose gel (1%) electrophoresis, and the obtained about 6.0 kb DNA fragment was recovered. The both fragments were ligated to give RBP4-His expression plasmid pcDNA3.1(+)/hRBP4-His wherein His tag is added to the C-terminal of human RBP4.

1C: Preparation of Human RBP4-his

Human RBP4-His was expressed using FreeStyle 293 expression system (Invitrogen) and expression plasmid pcDNA3.1(+)/hRBP4-His prepared in the above-mentioned 1B. According to the protocol attached to the FreeStyle 293 expression system, 600 mL of culture medium was used for expression. After transfection and 3 days of culture, the culture supernatant containing secreted hRBP4-His was recovered. The culture supernatant was repeatedly concentrated using VIVACELL 250 (molecular weight cutoff 10K, VIVASCIENCE), and diluted with 20 mM Tris (pH 8), whereby the buffer was substituted. The liquid was adsorbed by passage through TOYOPEARL DEAE-650 M column (1 cm ID×10 cm, Tosoh Corporation) equilibrated with 20 mM Tris buffer (pH 8) at a flow rate of 2.5 mL/min, and eluted at 0 to 0.35 M NaCl gradient to give human RBP4-His fractions. These fractions were concentrated to about 5 mL using Vivaspin 20 (molecular weight cutoff 10K, VIVASCIENCE). The Concentrated solution was passed through HiLoad 26/60 Superdex 200 pg column (2.6 cm ID×60 cm, GE Healthcare) equilibrated with TBS (pH 7.4), and eluted with TBS (pH 7.4). The fraction containing human RBP4-His was recovered, and concentrated to about 8 mL using Vivaspin 20 (molecular weight cutoff 10K, VIVASCIENCE). About 8 mg of human RBP4-His was obtained from 600 mL of the culture medium.

1D: Preparation of Human TTR

Human TTR was expressed using FreeStyle 293 expression system (Invitrogen) and expression plasmid pcDNA3.1(+)/hTTR prepared in the above-mentioned 1A. According to the protocol attached to the FreeStyle 293 expression system, 600 mL of culture medium was used for expression. After transfection and 3 days of culture, the culture supernatant containing secreted human TTR was recovered. The culture supernatant was repeatedly concentrated using VIVACELL 250 (molecular weight cutoff 10K, VIVASCIENCE), and diluted with 20 mM Tris (pH 8), whereby the buffer was substituted. The liquid was adsorbed by passage through TOYOPEARL DEAE-650 M column (1 cm ID×10 cm, Tosoh Corporation) equilibrated with 20 mM Tris buffer (pH 8) at a flow rate of 2.5 mL/min, and eluted at 0 to 0.55 M NaCl gradient to give human TTR fractions. These fractions were repeatedly concentrated using Vivaspin 20 (molecular weight cutoff 10K, VIVASCIENCE), and diluted with 20 mM Tris (pH 8), whereby the buffer was substituted. The liquid was adsorbed by passage through HiLoad Q Sepharose HP column (1.6 cm ID×10 cm, GE Healthcare) equilibrated with 20 mM Tris buffer (pH 8) at a flow rate of 1.0 mL/min, and eluted at 0 to 0.4 M NaCl gradient to give human TTR fractions. These fractions were concentrated to about 5 mL using Vivaspin 20 (molecular weight cutoff 10K, VIVASCIENCE). The Concentrated solution was passed through HiLoad 26/60 Superdex 75 pg column (2.6 cm ID×60 cm, GE Healthcare) equilibrated with PBS (pH 7.4), and eluted with TBS (pH 7.4). The fraction containing human TTR was recovered, and concentrated to about 5 mL using Vivaspin 20 (molecular weight cutoff 10K, VIVASCIENCE). About 6 mg of human TTR was obtained from 600 mL of the culture medium.

1E: Preparation of Human TTR-Biotin

Human TTR prepared in the above-mentioned 1D was labeled with biotin using Biotinylation Kit (Sulfo-Osu) (DOJINDO LABORATORIES) according to the attached protocol to prepare human TTR-biotin. Human TTR (5.0 mg) was repeatedly concentrated using Vivaspin 6 (molecular weight cutoff 10K, VIVASCIENCE) and diluted with 50 mM $NaHCO_3$, whereby the buffer was substituted. This solution was diluted with 50 mM $NaHCO_3$ to set the concentration of human TTR to 2.0 mg/mL, and aqueous Biotin-(AC5)2 Sulfo-OSu solution (10 mg/mL) (9.9 uL) was added and the mixture was reacted at 25° C. for 2 hr. The solution after the reaction was passed through NAP-25 column (GE Healthcare) equilibrated with PBS (pH 7.4), eluted with PBS (pH 7.4) and an eluate (3.5 mL) containing human TTR-biotin was recovered.

1F: Binding Assay by Retinol-RBP4-TTR ELISA

This ELISA system detects a complex with RBP4 and TTR based on the retinol dependent binding of RBP4 to TTR.

The His-tagged human RBP4 used was prepared in the above-mentioned 1C.

The biotinylated human TTR used was prepared in the above-mentioned 1E.

Streptavidin (20 μl) (10 μg/ml Streptavidin type II (Wako Pure Chemical Industries, Ltd.), 10 mM Tris-HCl (pH 7.5), 10 mM NaCl) was added to a 384 well blackplate (Nunc MaxiSorp, Thermo Fisher Scientific Inc.), and the plate was centrifuged (1000 rpm, 1 min) and coated at 4° C. overnight. The plate was washed twice with PBST (PBS, 0.05% Tween 20, 100 μl/well), and blocked with 25% Block Ace (Snow Brand Milk Products Co., Ltd., PBS, 100 μl/well). The plate was subjected to centrifugation (1000 rpm, 1 min), and incubated at room temperature for 4 hr or 4° C. overnight. The plate was washed twice with PBST (PBS, 0.05% Tween 20, 100 μl/well), and biotinylated human TTR (stock solution concentration 1.0 mg/ml) diluted 750-fold with PBST was added at μl/well. The plate was subjected to centrifugation (1000 rpm, 1 min), and further stood at room temperature for 1.5 hr or 4° C. overnight. The plate was washed 3 times with PBST (100 μl/well), and His-tagged human RBP4 (stock solution concentration 1.28 mg/ml) diluted 4000-fold with a reaction buffer (50 mM Tris-HCl, 150 mM NaCl, 0.005% Tween 20, 1 mM DTT, 0.1% BSA) was added at 10 μl/well. The dilution of the compound (200-fold concentration) was prepared with DMSO, and 1.6 μl each was added to a reaction buffer (320 μl) containing retinol (50 nM) (Sigma-Aldrich Co.). A reaction buffer (320 μl) containing retinol and added with DMSO was used as a positive control, and a reaction buffer (320 μl) not containing retinol and added with DMSO was used as a negative control. A mixed solution of retinol and the compound was added to the plate at 15 μl/well. The plate was stirred in a plate mixer, centrifuged (1000 rpm, 1 min), and reacted at room temperature for 2 hr. Anti-His HRP-conjugated antibody (QIAGEN) solution diluted with a reaction buffer was added at 10 μl/well, centrifuged (1000 rpm, 1 min), and reacted at room temperature for 30 min. The plate was washed 3 times with PBST (100 μl/well), SuperSignal ELISA Femto Maximum Sensitivity Substrate reagent (PIERCE, Thermo Fisher Scientific Inc.) was added at 30 μl/well, and the luminescence was measured by a plate reader (Envision).

The binding inhibitory activity of the compound was determined by 100×(positive control value−test compound value)/(positive control value−negative control value). The results are shown in Table 3.

TABLE 3

| Example No. | human RBP4 binding inhibitory activity (% at 10 μM) |
|---|---|
| Example 1 | 98 |
| Example 2 | 99 |
| Example 3 | 100 |
| Example 4 | 100 |
| Example 5 | 100 |

From the above-mentioned results, it was clarified that the compound of the present invention inhibits the binding of RBP4, and retinol and TTR.

Experimental Example 2

The blood RBP4-lowering action of the compound of the present invention was evaluated using C57BL/6J mouse.

Male 7- to 10-week-old C57BL/6J mice (Japan Charles River) were acclimation reared under free food ingestion conditions on CE-2 solid feed (CLEA Japan, Inc.) for 4 to 6 days, and randomly grouped (4 or 5 per group). On the day of the test, blood samples were collected from the tail vein, and plasma was separated (0 hr value). Thereafter, a test compound (Example 1, 2, 3, 4, 5, 6, 7 or 8) was orally administered at a dose of 3 mg/kg or 10 mg/kg (solvent: 0.5% methylcellulose solution (10 mL/kg)). At 8 and 24 hr after the compound was administered, blood samples were collected from the tail vein and plasma was separated. A 0.5% methylcellulose solution (10 mL/kg) was orally administered to the control group.

The amount of RBP4 in the collected plasma was measured by the ELISA method. Using rabbit anti-mouse RBP4 polyclonal antibody (Hokudo Co., Ltd.), RBP4 was quantified by the following process. A 96 well ELISA plate was coated with 50 μg/mL antibody (100 μL), and stood at 4° C. overnight or at room temperature for 2 hr. After blocking with BlockAce (Dainippon Pharmaceutical Co., Ltd.), 100 μL of mouse RBP4 or sample was added and the plate was stood at room temperature for 2 hr, washed with PBS-0.5% Tween20, added with HRP-labeled anti-RBP4 antibody (prepared by labeling RBP4 polyclonal antibody (Hokudo Co., Ltd.) with HRP (DOJINDO LABORATORIES)) (100 μL), and stood at room temperature for 1 hr. After washing, TMB (Sigma) was added at room temperature for 20 min to allow for color development. The reaction was quenched with 2N sulfuric acid and the absorbance at A450 nm was measured by a platereader. Variation from the initial value of each individual was taken as the relative value to the control group (initial value/control value, %) at each time point. The results are shown below in mean±standard deviation (n=4 or 5).

TABLE 4

| | | RBP4 (initial value/control value %) | |
|---|---|---|---|
| Example No. | dose | 8 hr later | 24 hr later |
| 1 | 10 mg/kg | 37.25 ± 11.45 | 61.81 ± 14.79 |
| 2 | 10 mg/kg | 23.93 ± 5.84 | 64.87 ± 16.79 |
| 3 | 10 mg/kg | 20.70 ± 1.55 | 49.64 ± 10.48 |
| 4 | 3 mg/kg | 19.86 ± 11.85 | 54.29 ± 19.15 |
| 5 | 3 mg/kg | 32.14 ± 6.82 | 36.20 ± 1.87 |
| 6 | 10 mg/kg | 58.17 ± 8.61 | 79.70 ± 5.22 |
| 7 | 10 mg/kg | 43.66 ± 4.92 | 71.75 ± 8.77 |

All the above-mentioned compounds showed a lower value, by single oral administration, than the control group 8 hr after the administration. These results show that the compound of the present invention has a blood RBP4-lowering action.

Experimental Example 3

The suppressive action for accumulation of retinoid metabolite bis-retinoid N-retinylidene-N-retinylethanolamine (A2E) in the eyeball, of the compound of the present invention, was evaluated using ATP-binding cassette A4 knockout (ABCA4 KO) mouse. A2E is the major constituent component of Lipofuscin in the eyeball, and is involved in the onset and pathology progression in atrophic age-related macular degeneration and Stargardt's disease.

ABCA4 KO mouse was confirmed to show remarkable accumulation of A2E, Lipofuscin along with aging, and is known as an animal model of atrophic age-related macular degeneration and Stargardt's disease.

8-Week-old male ABCA4 KO mice were randomly grouped, and 0.5% methylcellulose solution was orally administered to the control group, and 0.5% methylcellulose suspension of a compound at a dose shown in the following Table was orally administered to the test compound group, each once per day at 10 mL/kg. Each group contained 6 or 7 mice. After repetitive administration for 8 or 12 weeks, eyeball was isolated under anesthesia.

In the eyeball, A2E was measured by the HPLC method. A2E reference standard was synthesized from all-trans retinal, ethanolamine in acetic acid-added ethanol. First, 0.3 mL of PBS and zirconia beads were added to the eyeball, and homogenate was prepared using Mixer Mill MM 300 (QIAGEN). A chloroform:methanol (2:1) solution (0.8 mL) was added and the mixture was stirred for min. The lower layer was separately taken in a different tube, the chloroform:methanol (2:1) solution (0.6 mL) was further added and the mixture was stirred for 5 min. The lower layer was combined with one separated earlier, and dried to solidness by blowing nitrogen gas. 0.05 mL of 85% acetonitrile solution was added and the mixture was stirred to give a measurement sample. For HPLC, Alliance e2695 and Photo diode array 2998 (PDA) (Waters) were used, and Empower 2 was used as an analysis software. The column used was Atlantis dC18 (3 μm, 3.9×150 mm) (Waters), and the column temperature was set to 40° C. As the mobile phase, a mixed solution of acetonitrile and distilled water (containing 0.1% trifluoroacetic acid) was used at 1 mL/min and, as the gradient conditions, acetonitrile concentration was raised from 85% to 100% over 15 min, and then immediately decreased to 85% and one sample was monitored for 20 min. Quantification was performed at ultraviolet absorbance at 440 nm by PDA.

TABLE 5

| Example No. | dose | A2E (% of control value) |
|---|---|---|
| 2 | 10 mg/kg | 77.63 ± 9.06 |
| 3 | 10 mg/kg | 73.90 ± 15.58 |
| 4 | 1 mg/kg | 79.47 ± 14.53 |
| 5 | 3 mg/kg | 59.10 ± 10.33 |

Repetitive administration of all the above-mentioned compounds suppressed accumulation of retinoid metabolite A2E in the eyeball of ABCA4 KO mouse.

Formulation Example 1 (Production of Capsule)

| 1) compound of Example 1 | 30 mg |
|---|---|
| 2) microcrystalline cellulose | 10 mg |
| 3) lactose | 19 mg |
| 4) magnesium stearate | 1 mg |
| total | 60 mg |

1), 2), 3) and 4) are mixed and filled in a gelatin capsule.

Formulation Example 2 (Production of Tablet)

| 1) compound of Example 1 | 30 g |
|---|---|
| 2) lactose | 50 g |
| 3) cornstarch | 15 g |
| 4) calcium carboxymethylcellulose | 44 g |
| 5) magnesium stearate | 1 g |
| 1000 tablets | 140 g in total |

The total amount of 1), 2), 3) and 30 g of 4) are kneaded with water, vacuum dried and sieved. The sieved powder is mixed with 14 g of 4) and 1 g of 5), and the mixture is punched by a tableting machine. In this way, 1000 tablets containing 30 mg of the compound of Example 1 per tablet are obtained.

Formulation Example 3 (Production of Ointment)

| 1) compound of Example 1 | 0.5 g |
|---|---|
| 2) liquid paraffin | 1 g |
| 3) white petrolatum | 98.5 g |
| total | 100 g |

1), 2) are thoroughly mixed in a mortar, 3) is gradually added with kneading to the total amount of 100 g. The obtained mixture is divided and filled in a tube to give an ointment.

Formulation Example 4 (Production of Eye Drop)

| 1) compound of Example 1 | 0.05 g |
|---|---|
| 2) boric acid | 1.2 g |
| 3) L-sodium glutamate | 0.2 g |
| 4) sodium edetate | 0.005 g |
| 5) dibutylhydroxytoluene | 0.005 g |
| 6) chlorobutanol | 0.1 g |
| 7) benzalkonium chloride (10 w/v %) | 0.05 mL |
| 8) l-menthol | 0.008 g |
| 9) macrogol 4000 | 0.4 g |
| 10) sodium hydroxide | q.s. |
| 11) sterile purified water | added to 100 mL |

The above-mentioned components are mixed to give an eye drop.

INDUSTRIAL APPLICABILITY

The compound of the present invention has a superior RBP4-lowering action, and is useful as a medicament for the prophylaxis or treatment of a disease or condition mediated by an increase in RBP4 or retinol supplied by RBP4 such as age-related macular degeneration, Stargardt's disease and the like.

This application is based on patent application No. 2014-217770 filed in Japan, the contents of which are incorporated in full herein by this reference.

SEQ ID NO: 1: PCR primer (RBPU)
SEQ ID NO: 2: PCR primer (RBPL)

SEQ ID NO: 3: PCR primer (TTRU)
SEQ ID NO: 4: PCR primer (TTRL)
SEQ ID NO: 5: PCR primer (CMVP)
SEQ ID NO: 6: PCR primer (RBPECO)
SEQ ID NO: 7: PCR primer (TTRECO)

SEQ ID NO: 8: oligonucleotide (HISENU) for producing synthetic gene segment containing His tag sequence
SEQ ID NO: 9: oligonucleotide (HISENL) for producing synthetic gene segment containing His tag sequence

The invention claimed is:

1. A method of preparing a compound represented by formula (I):

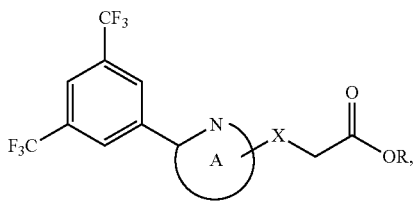

wherein ring A is a pyrazole ring, a pyridine ring, or a pyrimidine ring; X is $CH_2$ or O; and R is a hydrogen atom or a $C_{1-6}$ alkyl group;

the method comprising:

(a) performing an alkylation reaction; and (b) performing a hydrolysis reaction.

2. The method of claim 1, wherein the method comprises:

(a) performing the alkylation reaction to form a chemical bond with X; and (b) performing the hydrolysis reaction of an ester or nitrile group.

* * * * *